(12) United States Patent
Kawde et al.

(10) Patent No.: US 10,495,597 B2
(45) Date of Patent: *Dec. 3, 2019

(54) METHOD FOR DETECTING URIC ACID

(71) Applicant: KING FAHD UNIVERSITY OF PETROLEUM AND MINERALS, Dhahran (SA)

(72) Inventors: Abdel-Nasser Metwally Aly Kawde, Dhahran (SA); Nadeem Baig, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/177,836

(22) Filed: Nov. 1, 2018

(65) Prior Publication Data
US 2019/0137433 A1 May 9, 2019

Related U.S. Application Data

(63) Continuation of application No. 15/243,073, filed on Aug. 22, 2016, now Pat. No. 10,156,539.

(51) Int. Cl.
*G01N 27/30* (2006.01)
*G01N 27/48* (2006.01)
*C25D 9/08* (2006.01)

(52) U.S. Cl.
CPC .............. *G01N 27/308* (2013.01); *C25D 9/08* (2013.01); *G01N 27/48* (2013.01)

(58) Field of Classification Search
None
See application file for complete search history.

(56) References Cited

U.S. PATENT DOCUMENTS

| 8,608,922 B2 | 12/2013 | Papadimitrakopoulos et al. |
| 2015/0090601 A1 | 4/2015 | Kawde |

FOREIGN PATENT DOCUMENTS

| CN | 103604849 B | 9/2014 |
| KR | 10-2014-0113641 A | 9/2014 |

OTHER PUBLICATIONS

Zhonghua Xue, et al., "A green approach for assembling graphene films on different carbon-based substrates and their electrocatalysis toward nitrite", RSC Advances, vol. 5, 2015, pp. 36707-36714.

Jian Zhang, et al., "Scaly Graphene Oxide/Graphite Fiber Hybrid Electrodes for DNA Biosensors", Advanced Materials Interfaces, vol. 2, No. 1500072, Jul. 6, 2015, 6 pages.

Nadeem Baig, et al., "A novel, fast and cost effective graphene-modified graphite pencil electrode for trace quantification of L-tyrosine", Analytical Methods, vol. 7, 2015, pp. 9535-9541.

James Kariuki, et al., "Development of a Novel, Low-Cost, Disposable Wooden Pencil Graphite Electrode for Use in the Determination of Antioxidants and Other Biological Compounds", Sensors, vol. 15, 2015, pp. 18887-18900.

(Continued)

*Primary Examiner* — Eli S Mekhlin
(74) *Attorney, Agent, or Firm* — Oblon, McClelland, Maier & Neustadt, L.L.P.

(57) ABSTRACT

A modified graphite electrode comprising a coating of electrochemically reduced graphene oxide. The modified graphite electrode may be employed in detecting of uric acid. A sensing device comprising the modified graphite electrode and a method of making the modified graphite electrode are described herein.

3 Claims, 30 Drawing Sheets

(56) References Cited

OTHER PUBLICATIONS

Li et al., Sensors and Actuators B: Chemical, vol. 174, Nov. 2012, pp. 441-448.
Author Unknown, "Spray coating and spin coating of rGO thin film sheets, "Electronics World, posted Mar. 12, 2013 at https://www.printedelectronicsworld.com/articles/5228/spray-coating-and-spin-coating-of-rgo-thin-film-sheets and accessed on Mar. 9, 2018.
Lu et al., ACS Nano, vol. 2, No. 9, 1825-1832 (2008).
Borini et al., ACS Nano, vol. 7, No. 12, 11166-11173, 2013.

METHOD FOR DETECTING URIC ACID

CROSS-REFERENCE TO RELATED APPLICATIONS

The present application is a Continuation of 15/243,073, now allowed as U.S. Pat. No. 10,156,539 on Dec. 18, 2018, having a filing date of Aug. 22, 2016, the entire contents of which are incorporated herein by reference.

BACKGROUND OF THE INVENTION

Field of the Invention

This disclosure relates to a graphite electrode with an outer surface coated with electrochemically reduced graphene oxide, a method of making the graphite electrode, a device comprising the graphite electrode, and electrochemical quantification of analytes.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Graphene is a one-atom thick carbon sheet in which the carbon atoms are $sp^2$-hybridized and arranged in a hexagonal lattice (X. Huang, Z. Yin, S. Wu, X. Qi, Q. He, Q. Zhang, Q. Yan, F. Boey, H. Zhang, Small. 7 (2011) 1876-1902, incorporated herein by reference in its entirety). Due to its unique structural and physicochemical properties, it is widely used in different disciplines such as transparent conductors, energy storage devices, field emission display and nano-electronics (Y. Liu, X. Dong, P. Chen, Chem. Soc. Rev. 41 (2012) 2283-2307, incorporated herein by reference in its entirety). Graphene also has an excellent mechanical strength which is approximately 200 times more than steel (M. Pumera, A. Ambrosi, A. Bonanni, E. Chng, H. Poh, Trends Anal. Chem. 29 (2010) 954-965, incorporated herein by reference in its entirety). Graphene has extraordinary electrochemical properties including fast charge transfer, wide potential window and less resistance to charge transfer (S. Wu, Q. He, C. Tan, Y. Wang, H. Zhang, Small. 9 (2013) 1160-1172; and N. Baig, A.-N. Kawde, Anal. Methods. 7 (2015) 9535-9541, each incorporated herein by reference in their entirety). At room temperature, the electron mobility is 200000 $cm^2$ $V^{-1}s^{-1}$ and surface area is 2600 $m^2/g$ (T. Gan, S. Hu, Microchim. Acta. 175 (2011) 1-19, incorporated herein by reference in its entirety).

In view of the foregoing, one objective of the present disclosure is to provide a modified graphite electrode comprising a coating of electrochemically reduced graphene.

SUMMARY OF THE DISCLOSURE

The foregoing description is intended to provide a general introduction and summary of the present disclosure and is not intended to be limiting in its disclosure unless otherwise explicitly stated. The presently preferred embodiments, together with further advantages, will be best understood by reference to the following detailed description taken in conjunction with the accompanying drawings.

A first aspect of the disclosure relates to a modified graphite electrode, comprising a graphite electrode with an outer surface, and a coating on the outer surface of the graphite electrode, where the coating comprises electrochemically reduced graphene oxide, and the modified graphite electrode has an electroactive surface area in a range of 0.3-0.6 $cm^2$.

In one embodiment, the graphite electrode has an electroactive surface area in a range of 0.04-0.07 $cm^2$.

In one embodiment, the graphite electrode is in the form of a pencil lead.

In one embodiment, a thickness of the coating is in a range of 0.001-5 µm.

In one embodiment, the pencil lead has a diameter in a range of 0.1-1.4 mm, and a length in a range of 20-70 mm.

In one embodiment, the pencil lead is of a grade 6H, HB, B, or 4H.

A second aspect of the disclosure relates to a method for detecting uric acid, comprising: (i) immersing the modified graphite electrode of the first aspect, a reference electrode, and a counter electrode in an aqueous sample comprising 0.02-1,000 µM uric acid, and (ii) applying a square wave potential to the aqueous sample.

In one embodiment, the reference electrode is Ag/AgCl, and the counter electrode comprises platinum.

In one embodiment, the square wave potential has an amplitude in a range of 0.01-0.1 V, a frequency in a range of 10-100 Hz, and an adsorption time in a range of 10-240 s.

A third aspect of the disclosure relates to a device for sensing an analyte in a sample, comprising a reference electrode, a counter electrode, and the modified graphite electrode of the first aspect.

In one embodiment, the reference electrode is Ag/AgCl.

In one embodiment, the counter electrode comprises platinum.

The fourth aspect of the disclosure relates to a modified graphite electrode, comprising: (i) dispersing graphene oxide in a buffer to form a graphene oxide dispersion, (ii) immersing a graphite electrode with an outer surface, a reference electrode, and a counter electrode in the graphene oxide dispersion, and (iii) applying a cyclic potential to the graphene oxide dispersion to coat the outer surface of the graphite electrode with a coating comprising electrochemically reduced graphene oxide thereby forming the modified graphite electrode.

In one embodiment, a concentration of the graphene oxide in the graphene oxide dispersion is in a range of 1-5 mg/mL.

In one embodiment, the buffer is acetate buffer with a concentration in a range of 0.01-0.5 M.

In one embodiment, the reference electrode is Ag/AgCl.

In one embodiment, the counter electrode comprises platinum.

In one embodiment, the cyclic potential is applied at a scan rate of 10-120 mV/s from −1.4 V to 0.3 V for 3-10 cycles.

In one embodiment, the graphite electrode has an electroactive surface area in a range of 0.04-0.07 $cm^2$, a length in a range of 20-70 mm, is in the form of a pencil lead with a diameter in a range of from 0.1-1 mm, and of the type 6H, HB, F, B, or 4H.

In one embodiment, the modified graphite electrode has an electroactive surface area in a range of 0.3-0.6 $cm^2$, and a thickness of the coating is in a range of 0.001-5 µm.

DETAILED DESCRIPTION OF THE DISCLOSURE

Embodiments of the present disclosure will now be described more fully hereinafter with reference to the accompanying drawings, in which some, but not all embodiments of the disclosure are shown.

Within the description of this disclosure, where a numerical limit or range is stated, the endpoints are included unless stated otherwise. Also, all values and subranges within a numerical limit or range are specifically included as if explicitly written out. As used herein, the words "a" and "an" and the like carry the meaning of "one or more".

Figure 1A:
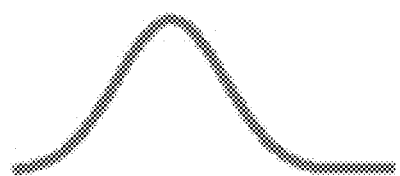
FIG. 1A shows the shape of the ridges on an embodiment of the modified graphite electrode.
Figure 1B:
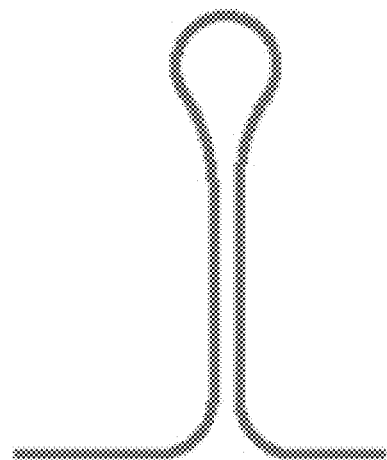
FIG. 1B shows the collapsed shape of the ridges on another embodiment of the modified graphite electrode.
Figure 1C:
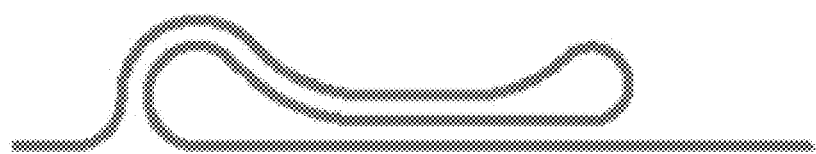
FIG. 1C shows the folded shape of the ridges on another embodiment of the modified graphite electrode.
Figure 1D:
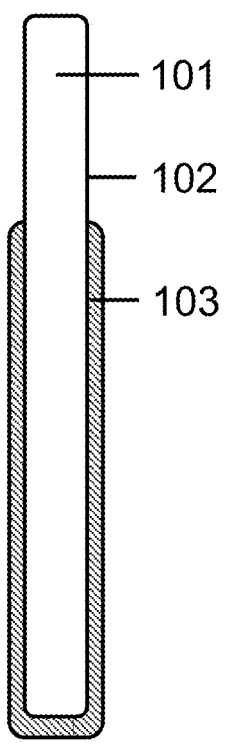
FIG. 1D is a drawing of an embodiment of the modified graphite electrode.
Figure 1E:
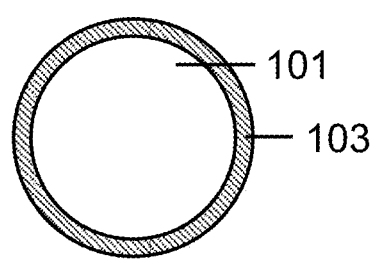
FIG. 1E is a cross-sectional view of an embodiment of the modified graphite electrode.

The first aspect of the disclosure relates to a modified graphite electrode comprising a graphite electrode 101 with an outer surface 102 and a coating 103 on the outer surface of the graphite electrode (FIGS. 1D and 1E). The coating comprises electrochemically reduced graphene oxide. In one embodiment, the coating consists of electrochemically reduced graphene oxide. In one embodiment, the modified graphite electrode has a distinct interface between the coating and the outer surface of the graphite electrode. In another embodiment, the modified graphite electrode has no distinct interface between the coating and the outer surface of the graphite electrode. Rather, the coating is integrated into or merged with the graphite substrate of the graphite electrode. Exemplary graphite electrodes include, but are not limited to, glassy carbon electrode, pyrolytic carbon electrode, carbon paste electrode, and pencil lead electrode. Preferably, the graphite electrode is a pencil lead electrode. The pencil lead is typically classified in terms of hardness grades. Hardness grades are associated on a hardness scale with the letter H or B or a combination of both, HB. Pencil lead of grades 9H, 6H, 4H, HB, B, or 8B may be used. A length of the pencil lead may range from 20-70 mm, preferably 40-70 mm, more preferably 45-65 mm. A diameter of the pencil lead may range from 0.13-1.40 mm, preferably 0.3-1 mm, more preferably 0.5-0.7 mm. The pencil lead may be made from beneficiated graphite, milled graphite, intercalated graphite, a graphite intercalation compound, such as $MC_8$ (M=K, Rb and Cs) and $M'C_6$ (M'=Li$^+$, Sr$^{2+}$, Ba$^{2+}$, Eu$^{2+}$, Yb$^{3+}$, and Ca$^{2+}$), graphite bisulfate, halogen-graphite compounds, and mixtures thereof. In a preferred embodiment, the graphite electrode is a mechanical pencil lead. In an alternative embodiment, the graphite electrode may be a pencil lead, for example, from a regular wooden or mechanical pencil. The wood casing may be removed with a knife until the pencil has a diameter of 3-6 mm, preferably 4-6 mm, more preferably 4.5-5.5 mm. One end of the wooden pencil may be removed by the knife to expose a pencil lead of a length ranging from 1-10 mm, preferably 1-5 mm, more preferably 2-3 mm. The pencil lead may then be polished, for example, with sandpaper and/or a polishing pad. In one embodiment, the graphite electrode is not a glassy carbon electrode. The graphite electrode has an electroactive surface area ranging from 0.040-0.070 cm$^2$, preferably 0.045-0.060 cm$^2$, more preferably 0.045-0.055 cm$^2$. The modified graphite electrode has an electroactive surface area ranging from 0.3-0.6 cm$^2$, preferably 0.3-0.5 cm$^2$, more preferably 0.3-0.4 cm$^2$. The electroactive surface area is calculated by the Randles-Sevcik equation:

$$I_p = 2.69 \times 10^5 n^{3/2} C\, A \gamma^{1/2} D^{1/2}$$

Where $I_p$ is the peak current, n is number of electrons participating in the redox reaction, C is analyte concentration (mol L$^{-1}$), A is the electroactive surface area (cm$^2$), $\gamma$ is the scan rate (V s$^{-1}$), and D is the diffusion coefficient (cm$^2$s$^{-1}$).

The modified graphite electrode may comprise 0.001-5 wt % of the coating, preferably 0.001-2 wt %, preferably 0.01-1 wt %, more preferably 0.05-1 wt %, based on a total weight of the modified graphite electrode. The coating may cover at least one end of the graphite electrode, and at least 50% of the outer surface area of the graphite electrode, preferably at least 70%, more preferably at least 90%. A thickness of the coating may range from 0.001-5 µm, preferably 0.001-1 µm, more preferably 0.001-0.1 µm. The thickness of the coating may taper from a first end of the coating to a second end of the coating. For example, the first end of the coating is thicker, and the thickness may range from 0.009-5 µm, preferably 0.5-5 µm, more preferably 1-5 µm. The second end of the coating is thinner, and the thickness may range from 0.001-2 µm, preferably 0.001-0.5 µm, more preferably 0.001-0.05 µm. In a preferred embodiment, the coating has a uniform thickness. A surface roughness of the coating may range from 1-10 nm, preferably 1-5 nm, more preferably 1-2 nm. A surface of the coating may comprise ridges. The ridges may cover up to 10% of the surface of the coating, preferably up to 30%, more preferably up to 60%. The ridges may be arranged in a substantially parallel manner relative to each other. As used herein, the term "substantially parallel" refers to the vast majority of the ridges are separated by substantially the same distance. For example, at least 60%, preferably at least 80%, more preferably at least 90% of the ridges may be aligned at no more than 10°, preferably no more than 7°, more preferably no more than 5°, relative to adjacent ridges. In some embodiments, the ridges have a shape shown in FIG. 1A. In other embodiments, the ridges have a collapsed shape shown in FIG. 1B. In an embodiment, the ridges have a folded shape shown in FIG. 1C. A width of the ridges may range from less than 1 nm to 200 nm, preferably 5-150 nm, preferably 10-100 nm, more preferably about 25-75 nm. Additionally, a height of the ridges (the distances from the base of the ridges to the top of the ridges) may range from 0.5-10 nm, preferably 0.9-8 nm, more preferably 2-6 nm. A length of a ridge may range from 0.5-40 µm, preferably 1-30 µm, more preferably 5-25 µm. A distance between successive ridges may range from 0.1-5 nm, preferably 0.1-3 nm, more preferably 0.5-2 nm.

The coating may comprise pores which may be sized to hold electrolyte ions, thus promoting diffusion of the electrolyte ions into the coating and thereby improving the performance of the modified graphite electrode. A size of the pores may range from 0.1-10 nm, preferably 0.1-5 nm, more preferably 0.1-2 nm. A porosity of the coating may range from 0.1-99.9%, preferably 1-30%, more preferably 20-30%. The thickness and the surface morphology of the coating may be studied by atomic force microscopy, scanning electron microscopy, transmission electron microscopy, and scanning tunneling microscopy.

The electrochemically reduced graphene oxide may be in the form of a flake or a sheet, preferably a sheet with a structure similar to that of graphene. The sheets of electrochemically reduced graphene oxide may be arranged in a substantially planar manner relative to each other so as to form a layered structure with 2-100 layers, preferably 2-60 layers, more preferably 2-30 layers. As used herein, the term "substantially planar" refers to the vast majority of the sheets within the coating are generally located within the same average plane or within substantially parallel planes. For example, at least 60%, preferably at least 80%, more preferably at least 90% of the electrochemically reduced graphene oxide sheets may be aligned along a major axis at no more than 10°, preferably no more than 7° more preferably no more than 5°, relative to adjacent sheets. The term "substantially planar" does not mean that the electrochemically reduced graphene oxide sheets per se are flat because at a molecular level, the sheets may have a corrugated or undulating configuration which leads to the aforementioned roughness of the coating. An interlayer distance may vary from 0.1-10 nm, preferably 0.5-5 nm, more preferably 0.5-2 nm.

In some embodiments, the graphene sheets covering the surface of the graphene-modified graphite pencil working electrode have an area of 0.2 mm$^2$ or greater, or 0.5 mm$^2$ or greater, or 0.8 mm$^2$ or greater, or 1 mm$^2$ or greater, or 1.5 mm$^2$ or greater, or 3 mm$^2$ or greater.

The reduced graphene oxide may be attracted to the outer surface of the graphite electrode by covalent interactions such as van der Waals' forces and π-π interactions.

The graphene oxide may be bought, prepared with the Hummers' method, or an improved Hummers' method known to those skilled in the art (D. C. Marcano et al. ACS Nano 4 (2010) 4806-4814, incorporated herein by reference in its entirety). Graphite, such as flake graphite, is oxidized to give graphite oxide that comprises at least one functional group with an oxygen atom such as a carbonyl group, a carboxyl group, or a hydroxyl group. In graphite oxide, the crystallinity of the graphite is impaired and the distance between layers is increased. Therefore, graphene oxide can be easily obtained by separation of the graphite oxide layers from each other by ultrasonication. An amount of oxygen in graphene oxide may be at least 50 wt %, preferably 50-70 wt %, more preferably 50-60 wt %, based on a total weight of graphene oxide. Graphene oxide may be reduced electrochemically thereby forming reduced graphene oxide and/or partially reduced graphene oxide. An amount of residual oxygen in the partially reduced graphene oxide may be between at least 20 wt % and not more than 50 wt %, preferably 25-40 wt %, more preferably 35-40 wt %, based on a total weight of the coating. An amount of residual oxygen in the reduced graphene oxide may be between at least 2 wt % and not more than 20 wt %, preferably 5-15 wt %, more preferably 5-10 wt %, based on the total weight of the coating. The amount of residual oxygen may be measured by X-ray photoelectron spectroscopy, energy-dispersive X-ray spectroscopy, and auger electron spectroscopy.

The modified graphite electrode may be utilized to detect analytes. As used herein, the term "analyte" refers to a substance that is (or whose chemical constituents are) being identified, detected, and/or measured by the modified graphite electrode. An analyte may be a component of a fluid (e.g., vapor or liquid) sample in which the modified graphite electrode is immersed. Exemplary analytes include, without limitation, uric acid, tyrosine (N. Baig, A. Kawde Anal. Methods, 7 (2015) 9535-9541, incorporated herein by reference in its entirety), biologically important catecholamines (tetrachlorohydroquinone, caffeic acid, rutin, p,p'-bisphenol, 3,4-dihydroxyphenylacetic acid, 3,4-di-t-butylcatechol, hydroquinone, catechol, isoproterenol, 3,4-dihydroxyephedrine, epinephrine, 3,4-dihydroxybenzylamine, dopamine, norepinephrine, 2,5-dihydroxybenzene-p-disulfonic acid), analytes of environmental interest, such as picric acid, 2,4-dinitrophenol, plunavin, trifluralin, 4-amino-2-nitrophenol, p-nitrophenol, p-nitroaniline, alkylphenols (4-methylthiophenol, 4-methylthio-o-cresol, carbofuran phenol, 2,3,6-trimethylphenol, 2,4-dimethylphenol, 2,3,5-trimethylphenol, 3,5-di-t-butylphenol, 4-methylphenol, 2-methylphenol, 2-isopropylphenol, phenol, terbutalin, and 3,5-dimethylphenol), and chlorophenols (2-benzyl-4-chlorophenol, 2,4,6-trichlorophenol, 2,3,4,6-tetrachlorophenol, 4-chloro-3,5-dimethylphenol, pentachlorophenol, 2,4-dichlorophenol, 2-chlorophenol, 4-chlorophenol, 2,4,5-trichlorophenol, 2,5-dichlorophenol, and 3-chlorophenol), biologically important analytes (glucose, lactate, oxygen, glutamate, choline, phosphate, acetylcholine, dioxybutyrate, homocysteine, D-cysteine, creatine, creatinine, sucrose, fructose, nitric oxide, galactose, arsenite, cholesterol, fructosamine, bilirubin, glycine, methionine, L-citrulline, phosphatidic acid, lysophosphatidic acid, arachidonic acid, asymmetric dimethylarginine, 1,3-diaminopropane, 21-deoxycortisol, aminoadipic acid, D-2-hydroxyglutaric acid, L-2-hydroxyglutaric acid, aminoadipic acid, 2-hydroxyadipic acid, oxoadipic acid, oxoglutaric acid, 7-hydroxyprogesterone, 3-hydroxyisovaleric acid, 3-hydroxymethylglutaric acid, 3-methylcrotonylglycine, 3-methylglutaconic acid, adipic acid, ammonia, methylglutaric acid, (S)-3-hydroxyisobutyric acid, 3-hydroxyisovaleric acid, 3-methylcrotonylglycine, 3-hydroxyisovaleric acid, pyruvic acid, (S)-3,4-dihydroxybutyric acid, pyroglutamic acid, ganglioside GM3, glucosylceramide, lactosylceramide, tetrahexosylceramide, trihexosylceramide, 2-hydroxyestradiol, 2-hydroxyestrone, 20-hydroxyeicosatetraenoic acid, 5-acetylamino-6-amino-3-methyluracil, alpha-N-phenylacetyl-L-glutamine, androstenedione, benzoic acid, bromide, cadaverine, cholic acid, coproporphyrin I, coproporphyrin III, deoxycholic acid, deoxycytidine, DHEA sulfate, DL-homocystine, estradiol, estriol, estrone, estrone sulfate, fluorine, glycocholic acid, guanine, hexanal hydroxyphenyllactic acid, iodide, L-aspartic acid, L-cysteine, L-glutamine, L-lactic acid, L-malic acid, L-methionine, malondialdehyde, myoinositol hexakisphosphate, N-acetylaspartylglutamic acid, orotidine, progesterone, salicyluric acid, selenomethionine, thymine, uric acid, vanilpyruvic acid, cortisol, anabasine, cotinine, hydroxycotinine, L(−)-nicotine pestanal nornicotine, heptacarboxylporphyrin I, enkephalin L, 24-hydroxycholesterol, 27-hydroxycholesterol, deoxyadenosine, 1-methyladenine, succinyladenosine, hexacosanoic acid, phytanic acid, pristanic acid, L-pipecolic acid, erucic acid, 7C-aglycone, 5C-aglycone, (R)-salsolinol, alpha-carotene, 5-methyltetrahydrofolic acid, butyric acid, mannitol meopterin, quinolinic acid, 2-butanol, acetone, butanone, ethanol, isopropyl alcohol, methanol, acetaldehyde, nicotinic acid, pantothenic acid, riboflavin, scyllitol, thiamine, honmogentisic acid, aminoadipic acid, L-histidine, 1,5-anhydrosorbitol, 1-methylhistidine, 3,4-dihydroxybenzeneacetic acid, 3-methylhistidine, 4-hydroxy-L-proline, 4-hydroxynonenal, 5-hydroxylysine, 8-hydroxyguanine, 8-hydroxyguanosine, anscrine, carnosine, citrulline, epsilon-(ganlilla-glutamyl)-lysine, folic acid, fumaric acid, galactitol, ganlilla-aminobutyric acid, glycerophosphocho line, glycylproline, hydroxyproline, L-2,4-diaminobutyric acid, L-alpha-aminobutyric acid, L-arabitol, L-arginine, L-asparagine, L-cystathionine, L-DOPA, L-glutamic acid, L-isoleucine, L-leucine, L-lysine, L-phenylalanine, L-proline, L-serine, L-threonine, L-tryptophan, L-valine, methylmalonic acid, myoinositol, pentosidine, phosphorylcholine, prolylhydroxyproline, ribitol, sorbitol, succinic acid, thiamine monophosphate, thiamine pyrophosphate, estriol-3-sulfate-16-glucuronide, estriol-3-glucuronide, acetylglycine, N-acetylserine, L-thyronine, prostaglandin E2, kynurenic acid, 24,25-dihydroxyvitamin D, 25,26-dihydroxyvitamin D, 25-hydroxyvitamin D2, calcidiol, ergocalciferol, vitamin D3, 11-dehydro-thromboxane B2, 5a-tetrahydrocortisol, ethylmalonic acid, FAD, flavin mononucleotide, glutaric acid, isovalerylglycine, liothyronine, suberic acid, tetrahydrocortisone, thyroxine, 3-hydroxybutyric acid, acetoacetic acid, isocitric acid, L-glutamic acid, L-malic acid, oxalacetic acid, indolcacetic acid, argininosuccinic acid, uracil, 3-methoxytyrosine, 5-mydroxyindoleacetic acid, homovanillic acid, N-acetyl-L-tyrosine, N-acetylvanilalanine, vanillylmandelic acid, vanylglycol, taurocyamine, aspartylglycosamine, 1,3,7-trimethyluric acid, 1,3-dimethyluric acid, 1,7-dimethyluric acid, 1-methylxanthine, 11b-PGF2a, 3-chlorotyrosine, 3-methylxanfhine, 5-HETE, 7-methylxanthine, caffeine, paraxanthine, theobromine, theophylline, iodotyrosine, dimethyl-L-arginine, 13S-hydroxyoctadecadienoic acid, symmetric dimethyl arginine, androstanediol, trans-trans -muconic acid, 2-methyl-3-hydroxybutyric acid, 2-methylacetoacetic acid, tiglylglycine, acetaminophen glucuronide, ubiquinol, dihydrothymine, urcidoisobutyric acid, chenodeoxycholic acid, chenodeoxycholic acid glycine conjugate, hyaluronic acid, taurochenodesoxycholic acid, taurocholic acid, 1b,3a,12a-trihydroxy-5b-cholanoic acid, hyocholic acid, hyodeoxycholic acid, ursodeoxycholic acid, isoursodeoxycholic acid, lithocholic acid, ursocholic acid, 2-methylcitric acid, 3-methyl-crotonylglycine, hydroxypropionic acid, 2-pyrrolidinone, dimethyl amine, 8-isoprostane, ascorbic acid, glutathione, o-phosphoethanolamine, 3,5-diiodothyronine, 1,3-diaminopropane, 1-methylguanosine, 16a-hydroxyestrone, enterodiol, enterolactone, N1-acetylspermidine, N8-acetyl-spermidine, perillic acid, perillyl alcohol, ribothymidine, xanthosine, testosterone, 1-methyluric acid, 3-methyladenine, citric acid, cytidine, hypoxanthine, inosine, N-acetyl-L-aspartic acid, orotic acid, oxidized glutathione, pseudouridine, thymidine, uridine, xanthine, 1-methylinosine, 16a-hydroxydehydroisoandrosterone, 5a-tetrahydrocorticosterone, alpha-linolenic acid, alpha-tocopherol, B-carotene, beta-cortol, docosahexaenoic acid, docosapentaenoic acid, gama-tocopherol, linoleic acid, lycopene, putrescine, tetrahydrodeoxycorticosterone, tetrahydrodeoxycortisol, vitamin A, L-fucose, prostaglandin F2a, leukotriene B4, 6-ketoprostaglandin F1a, sebacic acid, butyrylcamitine, decanoylcarnitine, dodecanoylcarnitine, isovalerylcamitine, L-hexanoylcamitine, L-octanoylcarnitine, L-palmitoylcarnitine, lactulose, propionylcarnitine, stearoylcarnitine, tiglylcamitine, dihydrouracil, 5-alpha-cholestanol, lathosterol, 1-methyladenosine, 3,5-diiodo-L-tyrosine, betaine, cyclic AMP, guanidine, guanidinosuccinic acid, guanidoacetic acid, methyl guanidine, picolinic acid, 2,3-butanediol, 2-hydroxyphenethylamine, 2-oxoarginine, 4-guanidinobutanoic acid, 7a-hydroxycholesterol, arginic acid, cholesterol sulfate, homo-L-arginine, methanethiol, p-octopamine, propylene glycol, sulfolithocholylglycine, tyramine, urea, L-kynurenine, beta-leucine, cob(I)alamin, inosinic acid, 16-a-hydroxypregnenolone, pyridinoline, histamine, lipoxin A4, hydrogen peroxide, thromboxane A2, D-xylose, 19-hydroxyandrost-4-ene-3,17-dione, glyceric acid, L-a-glutamyl-L-lysine, corticosterone, cortisone, 1-methylhistamine, (R)-3-hydroxybutyric acid, (R)-3-hydroxyisobutyric acid, (S)-3-hydroxyisobutyric acid, 1-butanol, 4-heptanone, D-Lactic acid, glycerol, hyaluronan, L-camitine, pyruvaldehyde, S-adenosylmethionine, hydrogen carbonate, ureidopropionic acid, beta-alanine, cortol, cortolone, leukotriene C4, leukotriene E4, adenosine triphosphate, ADP, guanosine diphosphate, guanosine triphosphate, p-hydroxyphenylacetic acid, taurine, 2-methylbutyrylglycine, isobutyrylglycine, methylsuccinic acid, N-butyrylglycine, epitestosterone, thyroxine sulfate, etiocholanolone, diphenhydramine, 3-hydroxydodecanoic acid, diadenosine hexaphosphate, diadenosine pentaphosphate, diadenosine tetraphosphate, diadenosine triphosphate, xanthurenic acid, cyanocobalamin, pyridoxine, hydrogen sulfide, thiosulfate, aldosterone 18-glucuronide, p-synephrine, m-tyramine, serotonin, 1-naphthol, 2-naphthol, retinyl ester, 2-pyrocatechuic acid, gentisic acid, dopamine glucuronide, isomaltose, melanin, N2,N2-dimethylguanosine, phenylacetic acid, trimethylamine N-oxide), and mixtures thereof.

Preferably, the analyte is uric acid. In the human body, uric acid is produced by the oxidation of purine (R. Goyal, V. Gupta, A. Sangal, N. Bachheti, Electroanalysis. 17 (2005) 2217-2223, incorporated herein by reference in its entirety). It is an important biomarker for certain diseases. Uric acid is present in the urine, serum, and blood. It is mainly excreted from the body with the help of the kidney. An abnormal level of uric acid in the body is responsible for a number of diseases such as Lesch/Nyhan syndrome and hyperuricemia, which could cause gout (R. Goyal, V. Gupta, A. Sangal, N. Bachheti, Electroanalysis. 17 (2005) 2217-2223, incorporated herein by reference in its entirety). A high concentration of the uric acid causes cardiovascular disease and kidney damage (R. Goyal, V. Gupta, A. Sangal, N. Bachheti, Electroanalysis. 17 (2005) 2217-2223, incorporated herein by reference in its entirety). The risk of diabetes mellitus is high in patients with a high concentration of uric acid (A. Costa, I. Iguala, J. Bedini, L. Quinto, I. Conget, Metabolism. 51 (2002) 372-375, incoporated herein by reference in its entirety). Therefore, the quantification of uric acid is highly important. A major problem in the electrochemical quantification of uric acid is the interference of the ascorbic acid, which has an oxidation potential similar to that of uric acid (J. He, G. Jin, Q. Chen, Y. Wang, Anal. Chim. Acta. 585 (2007) 337-343, incorporated herein by reference in its entirety).

Therefore, the second aspect of the disclosure relates to a method of detecting uric acid, comprising immersing the modified graphite electrode, a reference electrode, and a counter electrode in an aqueous sample comprising uric acid, and applying a square wave potential to the aqueous sample. A concentration of the uric acid may fall within a linear response curve of the modified graphite electrode and may range from 0.02-1,000 µM, preferably 0.2-0.5 µM, more preferably 0.2-0.22 µM.

The reference electrode may be a standard hydrogen electrode, a normal hydrogen electrode, a reversible hydrogen electrode, a saturated calomel electrode, a silver chloride (Ag/AgCl) electrode, or a dynamic hydrogen electrode. Preferably, the reference electrode is a silver chloride electrode. The counter electrode may comprise platinum, gold, or carbon. Preferably, the counter electrode is a platinum wire.

Preferably, the at least one end of the modified graphite electrode coated with electrochemically reduced graphene oxide may be in contact with the aqueous sample. The modified graphite electrode is in electrical communication with the reference electrode. A potential is applied between the reference electrode and the modified graphite electrode to produce a current. Changes in the current as a result of reduction/oxidation/decomposition of detected analytes (e.g. uric acid) can be used to determine the amount of analyte in the sample into which the electrode is placed. The biasing potential may have the waveform of a linear sweep voltammetry, square wave voltammetry, or a cyclic voltammetry. Preferably, square wave voltammetry is used, and the waveform may have an amplitude ranging from 0.01-0.1 V, preferably 0.01-0.05 V, more preferably 0.01-0.03 V. A frequency of the square wave voltammetry waveform may range from 10-100 Hz, preferably 30-60 Hz, more preferably 45-60 Hz. An adsorption time ranges from 10-240 s, preferably 50-180 s, more preferably 90-160 s. The modified graphite electrode may be reusable and may be capable of repeated detection without calibration or replacement.

The presence of biomolecules and common ions mostly does not interfere with the detection of uric acid in the solution using the disclosed method. Exemplary biomolecules include, without limitation, phenylalanine, alanine, glucose, fructose, L-methionine, and ascorbic acid. Exemplary common ions include, without limitation, $Na^+$, $K^+$, $Li^+$, $Ni^{2+}$, $SO_4^{2-}$, and $Cl^-$. Because of no or low interference from other molecules, the method can be used to detect uric acid in various samples such as whole blood, plasma, serum, saliva, sweat, urine, washes of tissues, extracts of tissues, amniotic fluid, and placental fluid.

The third aspect of the disclosure relates to a sensing device. The modified graphite electrode may be part of (e.g. integrated in) the sensing device which comprises the aforementioned reference electrode and counter electrode. The sensing device may include a housing that comprises at least one modified graphite electrode, and a fluid distribution manifold that comprises a fluid flow path that is in fluid communication with the modified graphite electrode, the counter electrode, and the reference electrode. The fluid flow path can bring a fluid comprising at least one analyte in contact with the modified graphite electrode for sensing.

The sensing device may be in communication with at least one readout device that may generally be capable of measuring the current and/or potential at the modified graphite electrode. In most embodiments, the readout device may be a set of electronics. An electronic readout device, for example, may be capable of detecting current changes. Moreover, the readout device may be a component of the sensing device or may be separated from the sensing device. Furthermore, the readout device may also be linked to an adapter that can interface with a controller device. Preferably, a readout circuit used to enable determination of the presence and/or amount of analyte may form part of the readout device. In some embodiments, the readout circuit may be configured to measure the current and/or the potential at the modified graphite electrode. The readout circuit may also be configured to indicate the current and/or potential value(s) to a user of the sensing device such that he/she can detect the presence of the analyte and quantify it based on this measurement. To achieve this, the readout circuit may comprise an electronic display and/or a loudspeaker for presenting the current and/or potential value(s) to the user, and may further comprise a transmitter (or transceiver) for transmitting the data to another device. The latter feature enables the user to monitor the environment from a remote location. In another embodiment, the readout circuit may be configured to determine the presence and/or amount of analyte using the current and/or potential value(s) and indicate the result to the user (with or without the current and/or potential value(s)). This embodiment therefore provides the user with the end result without requiring him/her to derive it from the raw data.

In practice, this analysis would be performed by the processor in combination with a storage medium. For example, a processor may be configured to receive the current and/or potential value(s) from the readout circuit and compare this with predetermined calibration data (e.g. predetermined measurements of current and/or potential difference versus analyte concentration) from the storage medium to determine the presence and/or amount of analyte.

The fourth aspect of the disclosure relates to a method of making the modified graphite electrode comprising: (i) dispersing graphene oxide in a buffer to form a graphene oxide dispersion, (ii) immersing a graphite electrode, a reference electrode, and a counter electrode in the graphene oxide dispersion, and (iii) applying a cyclic potential to the graphene oxide dispersion to coat an outer surface of the graphite electrode with a coating comprising electrochemically reduced graphene oxide thereby forming the modified graphite electrode.

The graphene oxide dispersion may be prepared by dispersing graphene oxide in the buffer by sonicating for 0.5-5 hours, preferably 1-4 hours, more preferably 1-3 hours. A concentration of the graphene oxide in the graphene oxide dispersion ranges from 1.0-5.0 mg/ml, preferably 2.0-4.0 mg/ml, more preferably 2.5-3.5 mg/ml. The buffer may be a citrate buffer, a phthalate buffer, or an acetate buffer, preferably an acetate buffer. A concentration of the buffer may range from 0.01-0.50 M, preferably 0.05-0.20 M, more preferably 0.05-0.15 M. A pH of the buffer may range from 4.0-5.0, preferably 4.5-5.0, more preferably 4.7-4.9.

The graphite electrode may be polished before it is immersed into the graphene oxide dispersion. For example, the graphite electrode can be polished with alumina particles with a size ranging from 0.05-0.5 µm, preferably 0.1-0.5 µm, more preferably 0.2-0.3 µm. The outer surface of the graphite electrode may be rinsed with solvents, such as ethanol, acetone, and water, to remove impurities. A length of the graphite electrode immersed in the graphene oxide dispersion may range from 20-70 mm, preferably 40-70 mm, more preferably 45-50 mm.

The cyclic potential may range from −1.6 V to 0.6 V, preferably −1.5 V to 0.4 V, more preferably −1.4 V to 0.3 V. The scan rate may range from 10-120 mV/s, preferably 50-120 mV/s, more preferably 90-110 mV/s. A number of cycles may vary from 3-10, preferably 4-10, more preferably 4-6. The whole process may take up to 60 minutes, preferably up to 40 minutes, more preferably up to 30 minutes.

The present embodiments are being described with reference to specific example embodiments and are included to illustrate but not limit the scope of the invention.

EXAMPLE 1

Materials and Methods

Uric acid, ascorbic acid, L-methionine, glucose, fructose, sodium chloride and potassium chloride were obtained from Sigma-Aldrich (USA). Sodium phosphate monobasic and di-potassium hydrogen orthophosphate was received from BDH (England). Alanine and L-phenylalanine were obtained from Fluka (USA). Graphite was received from Fischer Science Education (USA). Double distilled water was used for solution preparation and experimental work. The double distilled water was collected directly from Water Still Aquatron A 4000 D (UK).

Square wave voltammetry, cyclic voltammetry, and electrochemical impedance spectroscopy experiments were performed using a three-electrode system electrochemical workstation (Auto Lab, Netherland). The working electrode was the bare graphite pencil electrode (GPE) or the modified graphite electrode (dERGO-GPE), the counter electrode was a platinum wire, and Ag/AgCl was used as reference electrode. The GPE, reference and counter electrodes were fixed vertically, and about 7 mm of the GPE was dipped into the analytical solution. The GPE was previously described in detail (A. Kawde, M. Aziz, N. Baig, Y. Temerk, J. Electroanal. Chem. 740 (2015) 68-74, incorporated herein by reference in its entirety). All experiments were conducted in a 3-ml glass cell. GR-2000 electrical balance was used for the measurements of all weights. Accumet® XL50 pH meter was used for the control of the buffers pH. FE-SEM images of the bare GPE and dERGO-GPE were recorded using TESCAN LYRA 3 (Brno, Czech Republic) at the Center of Research Excellence in Nanotechnology, KFUPM. Raman and FTIR spectra of the graphite and graphene oxide were collected by HORIBA Scientific LabRAM HR Evolution and NICOLET 6700 FT-IR, respectively.

EXAMPLE 2

Characterization of Graphene Oxide (GO)

Figure 1F:
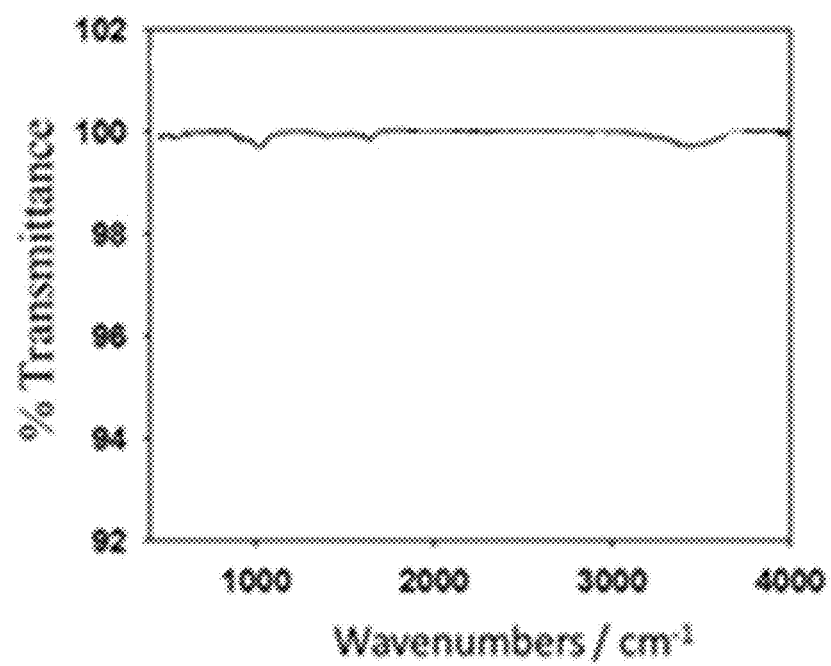
FIG. 1F is a Fourier transform infrared spectrum of graphite.
Figure 2:
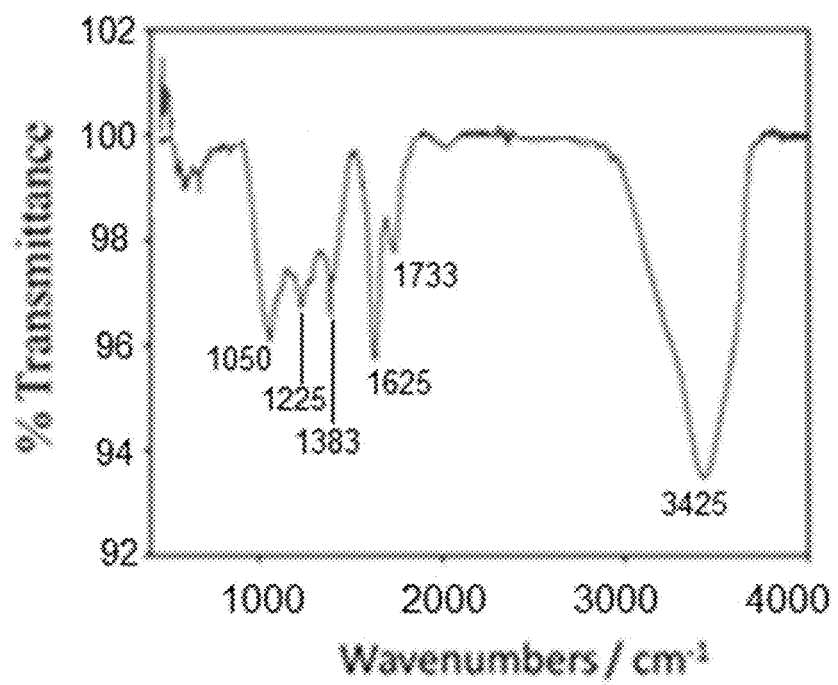
FIG. 2 is a Fourier transform infrared spectrum of graphene oxide.
Figure 3:
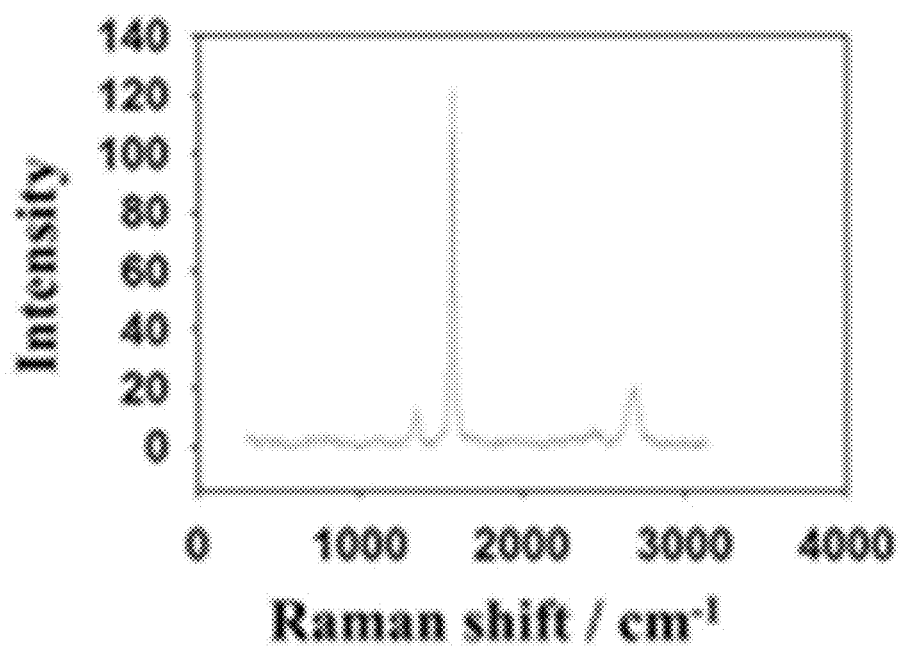
FIG. 3 is a Raman spectrum of graphite.
Figure 4:
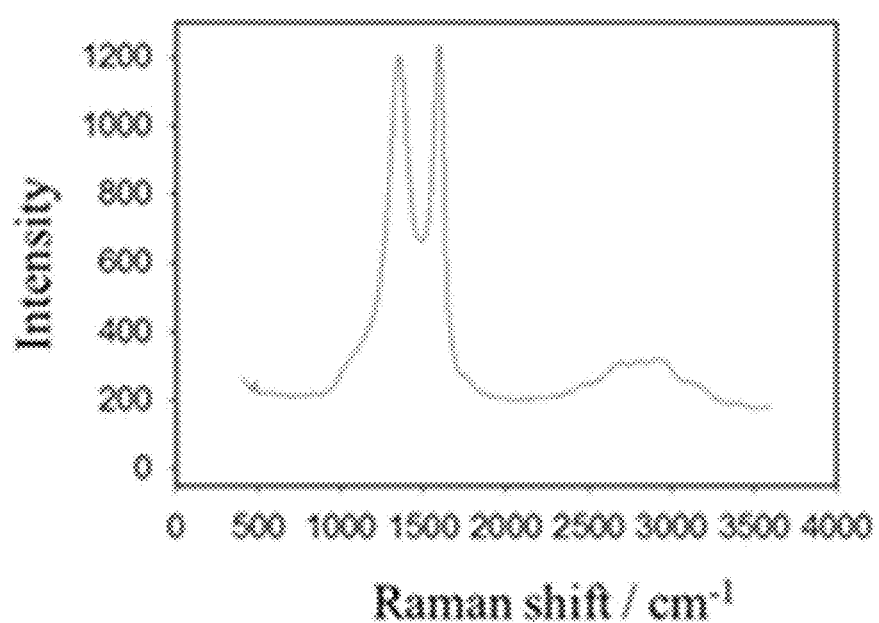
FIG. 4 is a Raman spectrum of graphene oxide.
Figure 5:
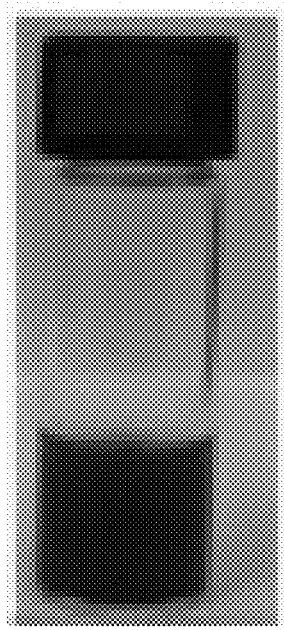
FIG. 5 shows a dispersion of graphite.
Figure 6:
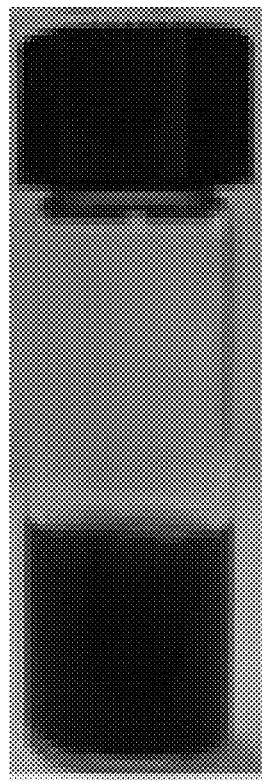
FIG. 6 shows a dispersion of graphene oxide.

GO was prepared by the Hummers method. The synthesized GO was characterized by the FT-IR. The FT-IR spectrum (FIG. 2) indicated the presence of hydroxyl group ($v=3425$ cm$^{-1}$), carboxyl carbonyl ($v=1733$ cm$^{-1}$), aromatic carbon-carbon double bond ($v=1625$ cm$^{-1}$), carboxylic acid —C—O stretching ($v=1383$ cm$^{-1}$), epoxy —C—O stretching ($v=1225$ cm$^{-1}$), and alkoxy —C—O stretching ($v=1050$ cm$^{-1}$) (T. Yang, L. Liu, J. Liu, M.-L. Chen, J.-H. Wang, J. Mater. Chem. 22 (2012) 21909-21916, incorporated herein by reference in its entirety). The presence of these entire functional groups confirmed the formation of the dark brown graphene oxide (FIG. 6) from graphite (FIG. 5). The FT-IR spectra of graphite (FIG. 1F) did not show any significant peak. FIGS. 3 and 4 are the Raman spectra of graphite and synthesized graphene oxide, respectively. A weak D, 2D, and strong G-band was observed in the FIG. 3. On the other hand, graphene oxide Raman spectra (FIG. 4) revealed a prominent D and G band appeared at 1350 cm$^{-1}$ and 1594 cm$^{-1}$, respectively. A relative shift in D and G band of the graphene oxide was observed compared to the graphite (A. Alhwaige, T. Agag, H. Ishida, S. Qutubuddin, RSC Adv. 3 (2013) 16011-16020, incorporated herein by reference in its entirety).

EXAMPLE 3

Preparation of dERGO-GPE

The parameters affecting the preparation of dERGO-GPE were studied and advantageous conditions were listed in Table 1. A 3 mg/ml graphene oxide in 0.1 M acetate buffer (pH 4.8) solution was prepared and sonicated for 2 hours to obtain a uniform and stable dispersion. The dispersed graphene oxide was transferred into the 3-ml cell, and the GPE, reference and counter electrodes were immersed into the graphene oxide dispersion. The graphene oxide directly reduced onto the GPE surface when a cyclic potential swept at a scan rate of 20 mV/s from −1.4 V to 0.3 V over 5 cycles. The modified electrode was washed gently by dipping in the double distilled water prior to analysis.

Figure 7:
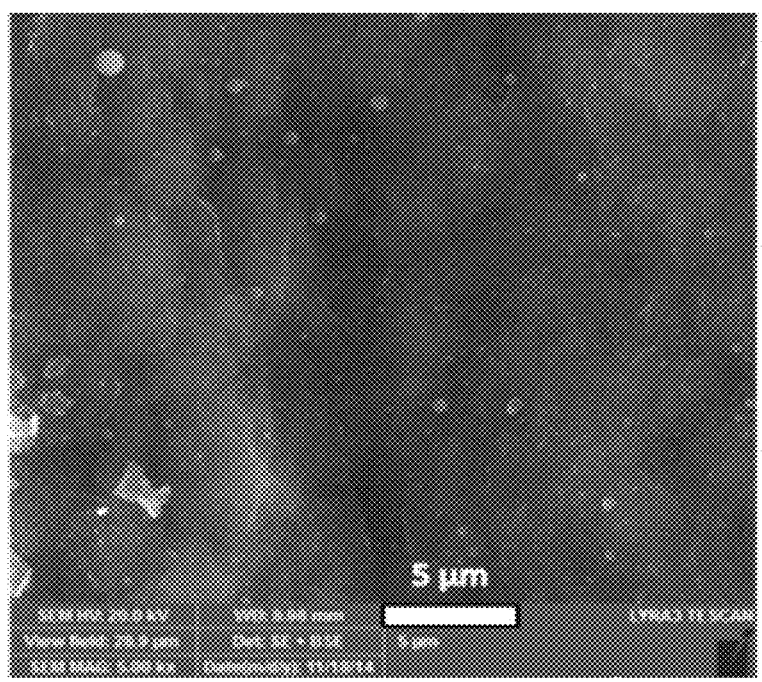
FIG. 7 is a micrograph of a bare graphite electrode at 5,000× magnification.
Figure 8:
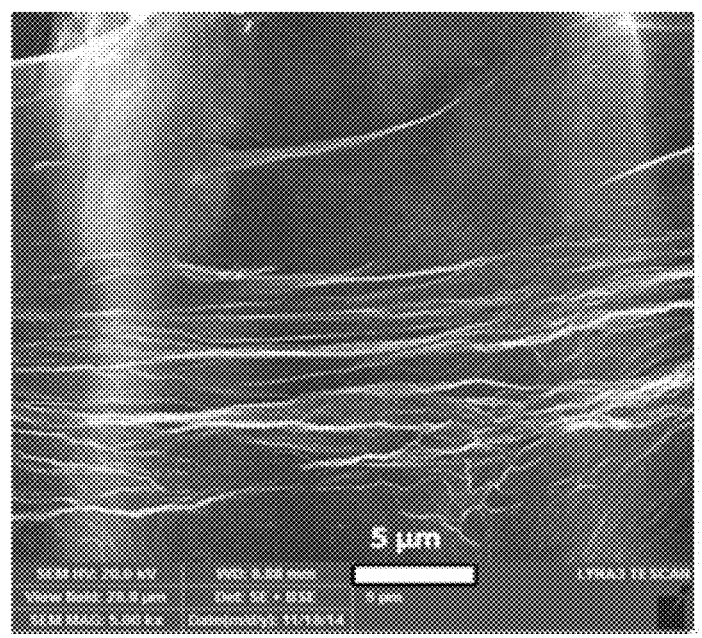
FIG. 8 is a micrograph of a modified graphite electrode at 5,000× magnification.
Figure 9:
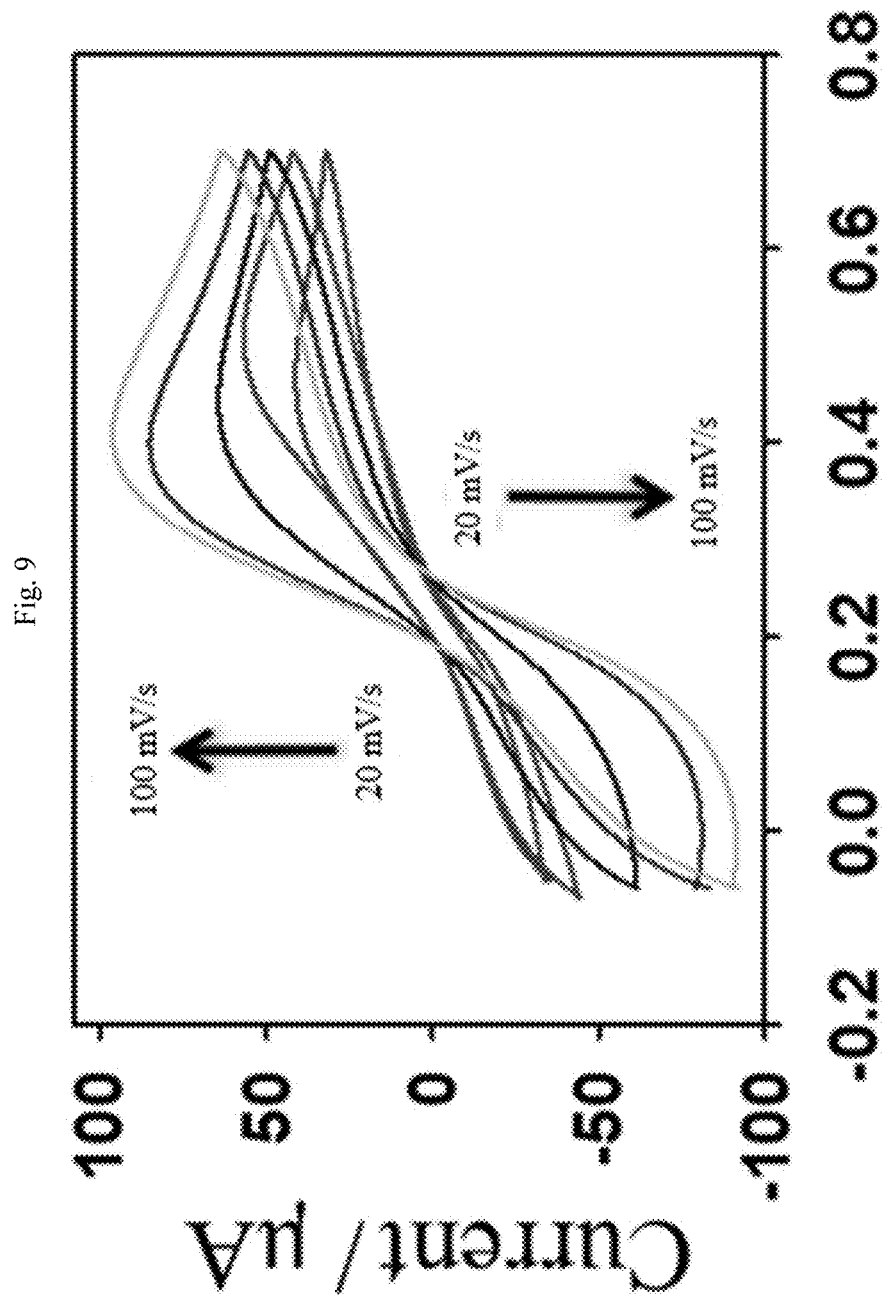
FIG. 9 is an overlay of cyclic voltammograms at a bare graphite electrode in a solution comprising 5 mM $K_3Fe(CN)_6/K_4Fe(CN)_6$ and 0.1 M KCl with scan rates of 20 mV/s, 40 mV/s, 60 mV/s, 80 mV/s, and 100 mV/s.

The morphology of the reduced GO was studied by FE-SEM. The presence of graphene layers was observed on the surface of the modified GPE (FIG. 8) compared to the bare GPE (FIG. 7) where no such layers are present. The presence of layers indicated GO has successfully reduced electrochemically on the GPE surface. Moreover, from FIG. 8, it could be observed the graphene sheets are wrinkled. The wrinkled graphene sheets not only provide the stability to not easily revert to the graphitic form and also increased the surface area (R. Kou, Y. Shao, D. Wang, M. Engelhard, J. Kwak, J. Wang, V. Viswanathan, C. Wang, Y. Lin, Y. Wang, I. Aksay, J. Liu, Electrochem. Commun. 11 (2009) 954-957, incorporated herein by reference in its entirety).

TABLE 1

Conditions for formation of dERGO-GPE (nos. 1-4) and analysis of uric acid (nos. 5 and 6)

| Sr # | Parameters | Best response |
|---|---|---|
| 1 | Scan rate for graphene reduction | 0.1 V/s |
| 2 | Graphene concentration | 3 mg/mL |
| 3 | Scan window for graphene oxide reduction | −1.4 V to 0.3 V |
| 4 | Scan number for graphene oxide reduction | 5 |
| 5 | Electrolyte | 0.1M PBS |
| 6 | Technique | SWV |

The parameters affecting the analysis of uric acid were studied, and it was found that an advantageous response was obtained with 0.1 M PBS and square wave voltammetry (SWV).

EXAMPLE 4

Figure 10:
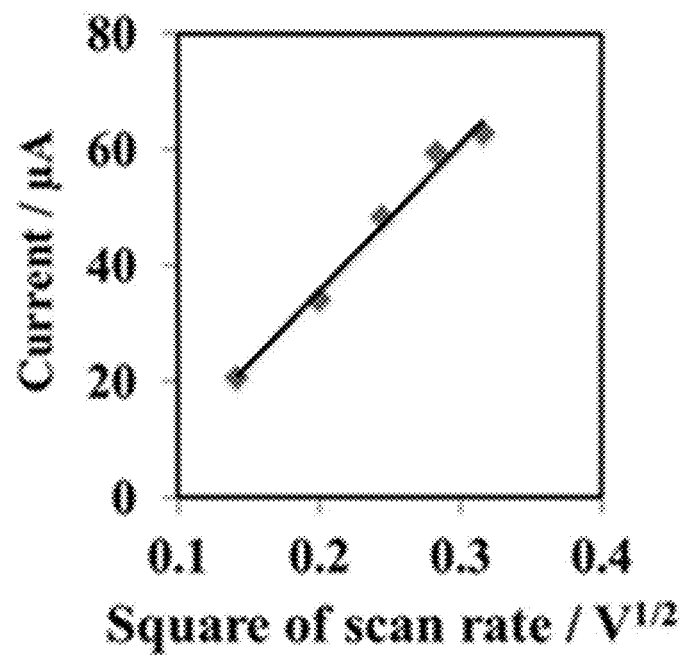
FIG. 10 shows a linear relationship between the peak current and the square root of the scan rate observed in FIG. 9.
Figure 11:
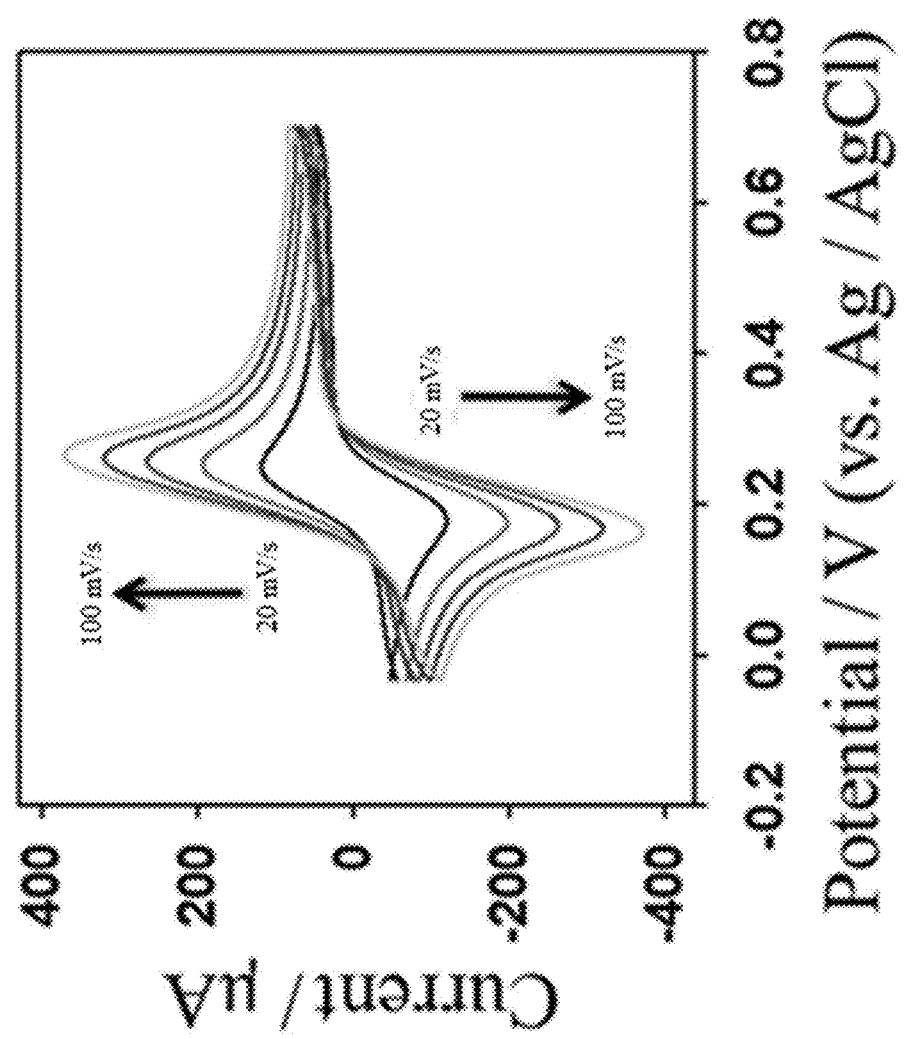
FIG. 11 is an overlay of cyclic voltammograms at a modified graphite electrode in a solution comprising 5 mM $K_3Fe(CN)_6/K_4Fe(CN)_6$ and 0.1 M KCl with scan rates of 20 mV/s, 40 mV/s, 60 mV/s, 80 mV/s, and 100 mV/s.
Figure 12:
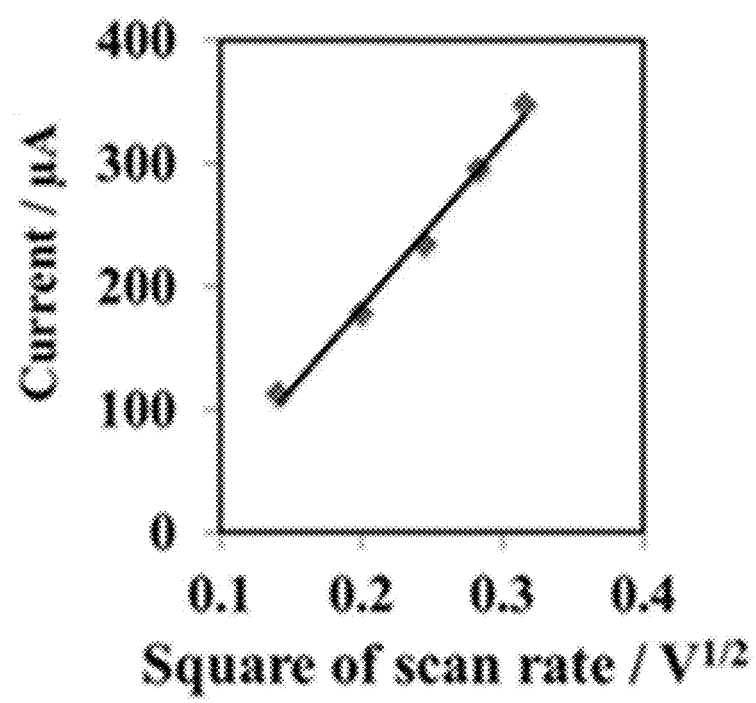
FIG. 12 shows a linear relationship between the peak current and the square root of the scan rate observed in FIG. 11.

Study of the Electroactive Surface Area and Electrochemical Behavior of dERGO-GPE In order to elucidate the electroactive behavior of the graphene on the GPE surface, the electroactive surface area of the dERGO-GPE and bare GPE was calculated by the Randles-Sevcik equation:

$$I_p = 2.69 \times 10^5 n^{3/2} C A \gamma^{1/2} D^{1/2}, \tag{1}$$

where n is electrons number participate in the redox reaction, C is analyte concentration in $molL^{-1}$, A is electrode electroactive surface area in $cm^2$, $\gamma$ is the scan rate in $Vs^{-1}$ and D represents diffusion coefficient in $cm^2 s^{-1}$. FIGS. 10 and 12 show the direct relation of peak current ($I_p$) and the square root of scan rate ($\gamma^{1/2}$). All other parameters n, C, and D in the Randles-Sevcik equation are constant. The electroactive surface area was calculated from equation 1 by sweeping the potential at a different rate from 20 mV/s to 100 mV/s in a solution containing 0.1 M KCl and 5 mM $K_3Fe(CN)_6/K_4Fe(CN)_6$. The electroactive surface area of bare GPE and dERGO-GPE was 0.0686 $cm^2$ and 0.3615 $cm^2$, respectively. This showed the graphene immensely affect the electroactive surface area of the GPE.

Figure 13:
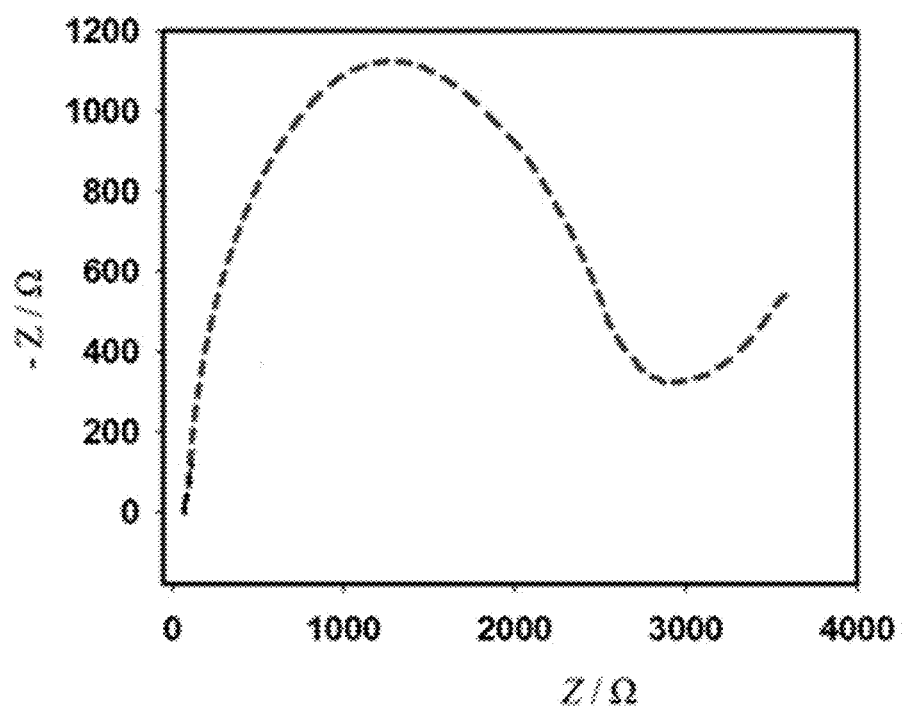
FIG. 13 is an electrochemical impedance spectrum of a bare graphite electrode in a solution comprising 5 mM $K_3Fe(CN)_6/K_4Fe(CN)_6$ and 0.1 M KCl.
Figure 14:
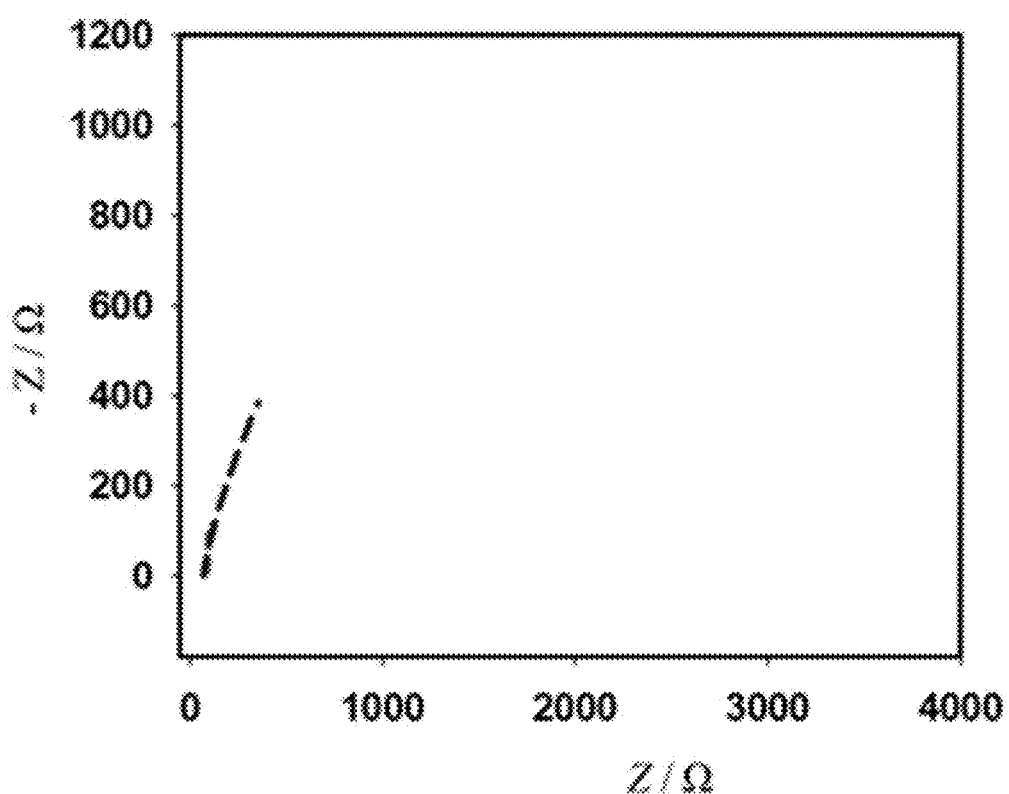
FIG. 14 is an electrochemical impedance spectrum of a modified graphite electrode in a solution comprising 5 mM $K_3Fe(CN)_6/K_4Fe(CN)_6$ and 0.1 M KCl.

The interface properties of the bare and dERGO-GPE were analyzed by using the electrochemical impedance spectroscopy, a 5 mV potential in the frequency range of 100 kHz to 0.01 Hz was applied to the working electrode. FIGS. 13 and 14 describe the electrochemical spectra of bare GPE (FIG. 13) and dERGO-GPE (FIG. 14) in a solution containing 5 mM $K_3Fe(CN)_6/K_4Fe(CN)_6$ and 0.1M KCl. The frequency for the electrochemical impedance spectra swept from 100 kHz and 0.01 Hz. The two axes −Z and Z indicate the imaginary and real value of the impedance variables, respectively. Nyquist plot consists of two parts: one is semicircle part and other is the straight line. The charge transfer resistance ($R_{ct}$) for bare GPE was 2954Ω and almost a straight line was observed for the dERGO-GPE. $R_{ct}$ values determined from the semicircle part and straight line of the impedance spectra correspond to the diffusion control process. The $R_{ct}$ value of the modified electrode was much less than the unmodified electrode. The low value of the $R_{ct}$ revealed the surface of the dERGO-GPE became more conductive due to the presence of graphene layers compared to the bare GPE.

Figure 15:
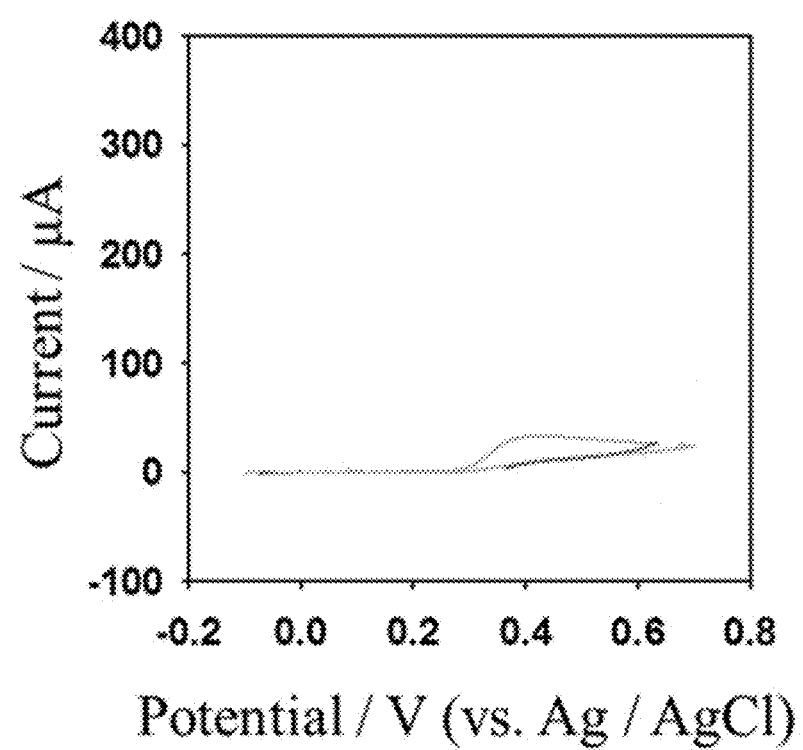
FIG. 15 is a cyclic voltammogram (scan rate: 100 mV s$^{-1}$) at a bare graphite electrode in a solution comprising 1 mM uric acid in a phosphate-buffered saline (PBS) buffer (0.1 M, pH 7.0).
Figure 16:
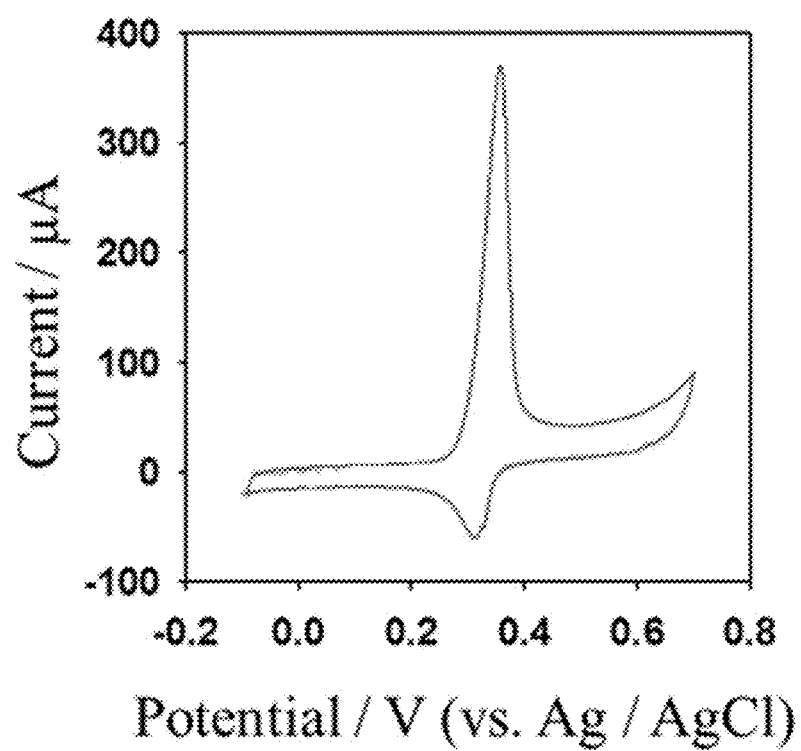
FIG. 16 is a cyclic voltammogram (scan rate: 100 mV s$^{-1}$) at a modified graphite electrode in a solution comprising 1 mM uric acid in a PBS buffer (0.1 M, pH 7.0).

FIGS. 15 and 16 compare the behavior of the bare GPE (FIG. 15) and dERGO-GPE (FIG. 16) for 1 mM uric acid in 0.1 M PBS buffer (pH 7.0) by cyclic voltammetry. A prominent sharp peak was observed on the voltammogram at dERGO-GPE whereas the voltammogram at GPE showed a broad peak. A significant increase in current was obtained with dERGO-GPE compared to the bare GPE. The uric acid oxidation peak on the bare and modified GPE appeared at 0.40 and 0.35 V, respectively.

The electrode surface plays a role in the reversibility and the kinetics of the electrochemical reaction. The cyclic voltammograms reveal the reversibility of the electrochemical reaction (T. Ndlovu, O. Arotiba, S. Sampath, R. Krause, B. Mamba, Int. J. Electrochem. Sci. 7 (2012) 9441-9453, incorporated herein by reference in its entirety). Equation 2 was used to calculate the potential difference between the anodic peak potential ($E_{pa}$) and the cathodic peak potential ($E_{pc}$) of the cyclic voltammograms of uric acid in 0.1 M PBS.

$$\Delta E = E_{pa} - E_{pc} = 59/n \tag{2}$$

In the case of irreversible reaction, only a single peak appears. The reaction is considered as reversible when the value of ΔE is 59/n mV and quasi-reversible if the value is greater than 59/n mV. The ΔE value calculated for the uric acid was 37 mV. The value was higher compared to the theoretical value 59/n mV which indicated the electrochemical reaction on the electrode surface was quasi-reversible. The cyclic voltammogram of bare electrode revealed the electrochemical reaction of the uric acid on the surface was irreversible, and no reduction peak was observed on bare GPE. This observation means that the reversibility of reduction/oxidation of the uric acid was feasible on the modified electrode surface. Moreover, the value of n calculated from equation 2 was 1.6. This value revealed the two electrons contributing to the electrochemical reaction of uric acid.

EXAMPLE 5

Effect of pH on the Oxidation Peak of Uric Acid at dERGO-GPE

Figure 17:
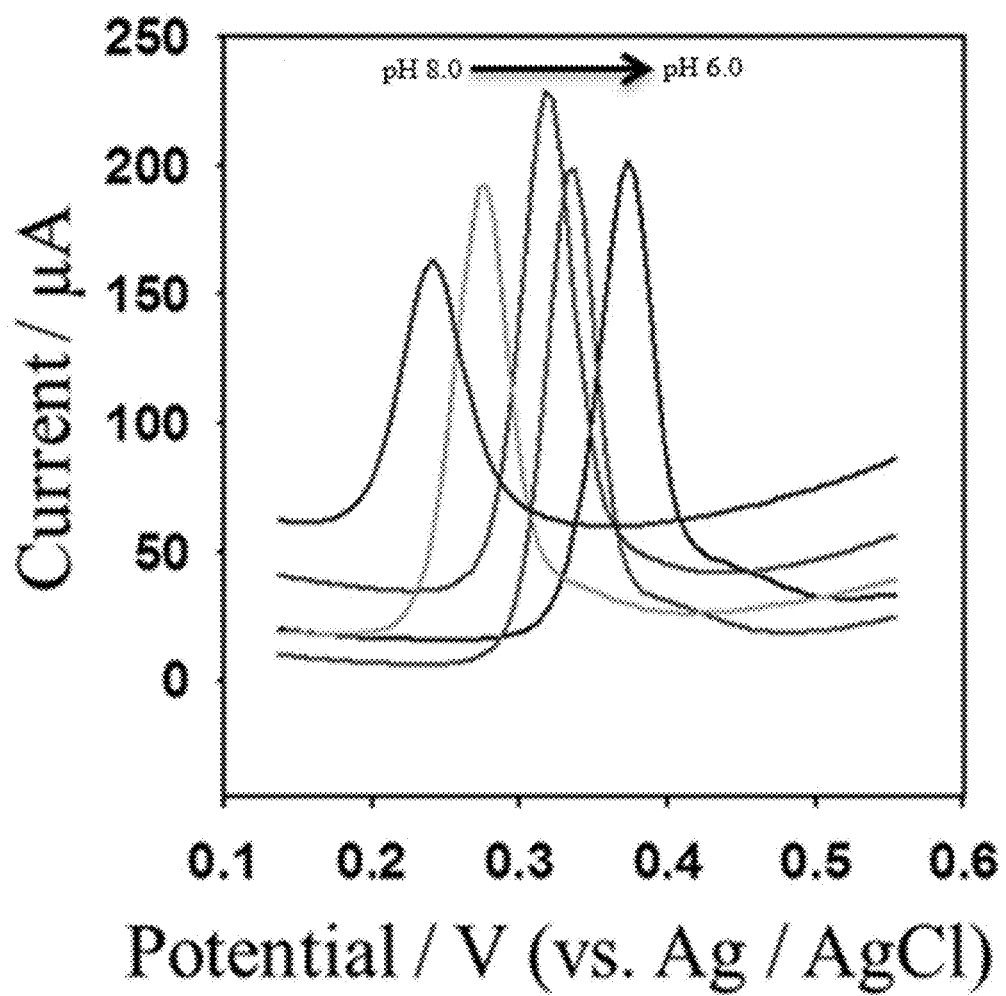
FIG. 17 is an overlay of square wave voltammograms at a modified graphite electrode in a solution comprising 10 μM uric acid in a PBS buffer (0.1 M) at pH 8.0, 7.5, 7.0, 6.5, and 6.0.
Figure 18:
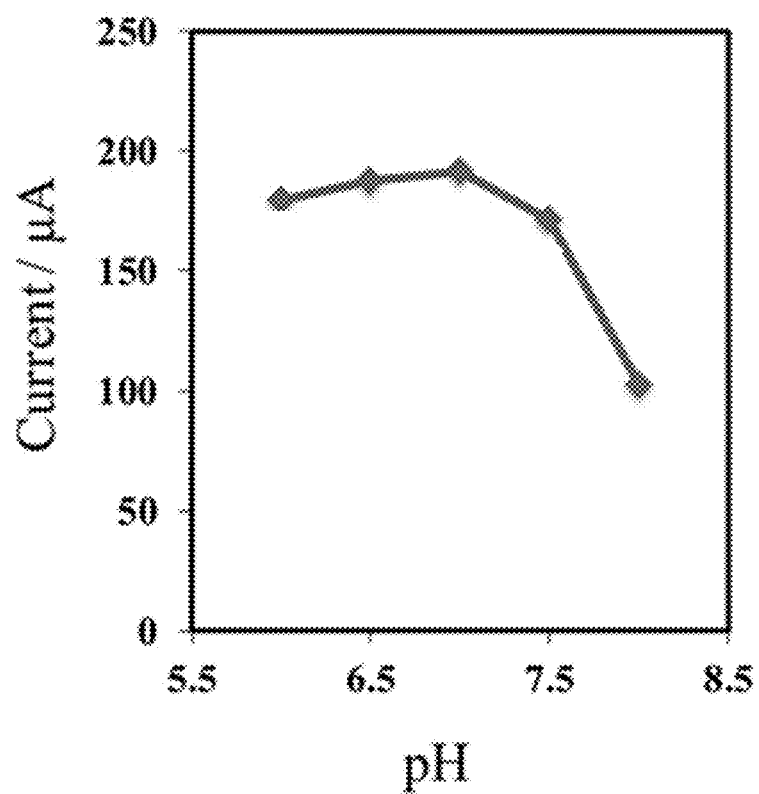
FIG. 18 is a plot of the peak currents versus the pH values observed in FIG. 17.
Figure 19:
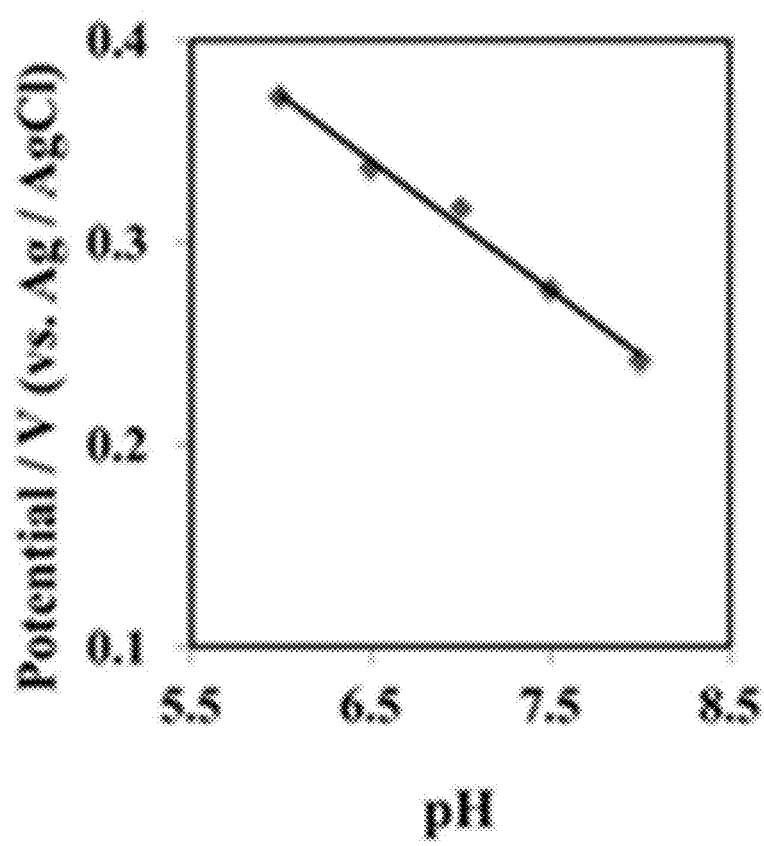
FIG. 19 shows a linear relationship between the pH value and the peak oxidation potential observed in FIG. 17.

The supporting electrolyte pH has a significant effect on the peak shift and also on peak current of the uric acid. The pH effect was scanned from 6.0 to 8.0 in a 0.1 M PBS buffer comprising 10 μM uric acid (FIG. 17). The oxidation peak current slightly increased as the pH increased and reached a maximum value at pH 7.0 and started decreasing after that. A linear negative shift in oxidation peak potential was observed as the pH is increased from the 6.0 to 8.0 (FIG. 19). Equation (3) represents the equation of the line shown in FIG. 19. The slope of the linear relation ($R^2=0.991$) between pH and uric acid oxidation peak potential was −64.5 mV and is very close to the theoretical value −59 my. It indicated an equal number of protons and electrons were involved in the electro-oxidation of the uric acid, which is in agreement with reported work (F. Zhang, Z. Wang, Y. Zhang, Z. Zheng, C. Wang, Y. Du, W. Ye, Talanta. 93 (2012) 320-325, incorporated herein by reference in its entirety).

$$E \text{ vs. Ag/AgCl} = 760.3 - 64.5 \text{ [pH]} \tag{3}$$

EXAMPLE 6

Investigation of Square Wave Voltammetry (SWV) Parameters

Figure 20:
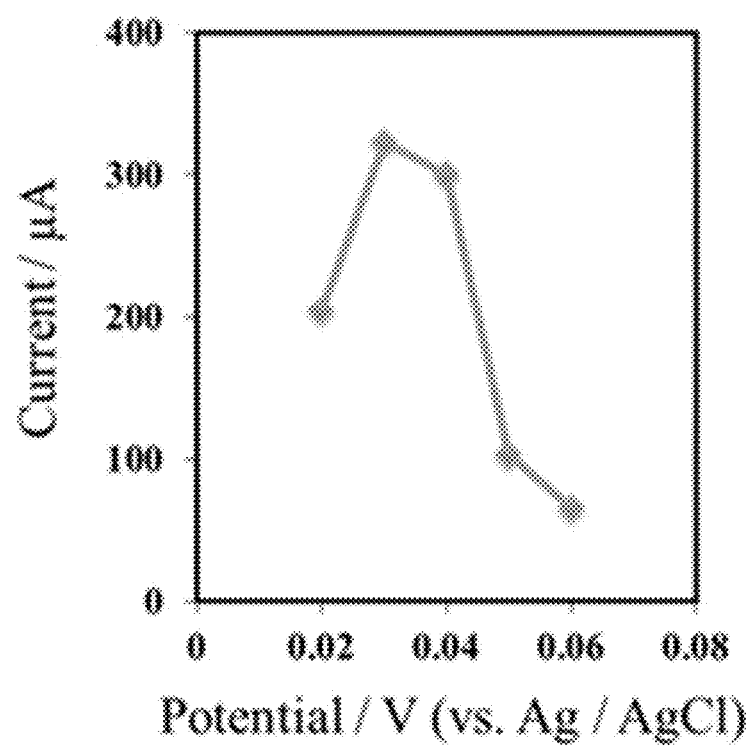
FIG. 20 shows a relationship between the current and the amplitude of the square wave potential at the modified graphite electrode in a sample comprising 10 μM uric acid in a PBS buffer (0.1 M, pH 7.0).
Figure 21:
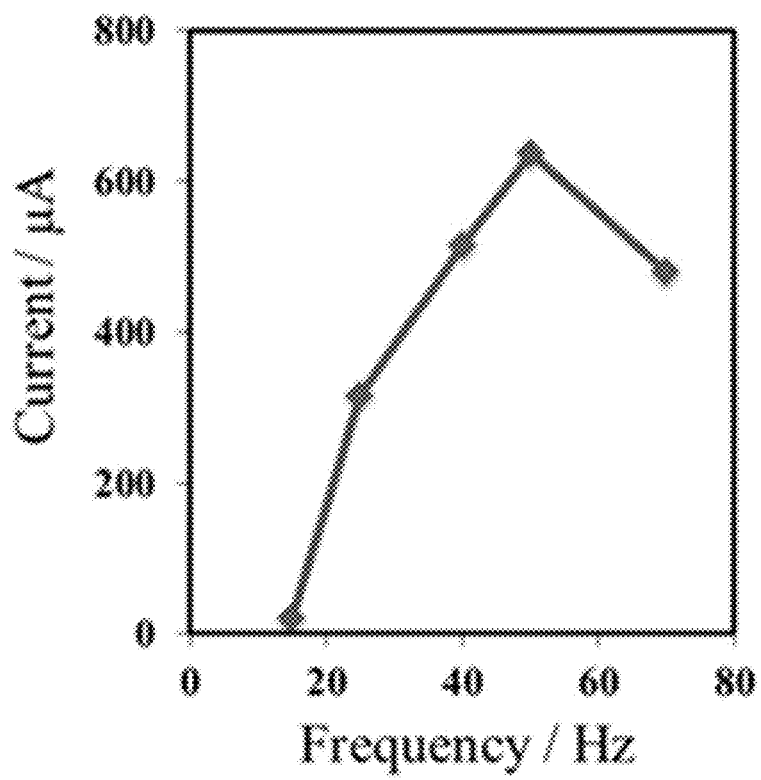
FIG. 21 shows a relationship between the current and the frequency of the square wave potential at the modified graphite electrode in a sample comprising 10 μM uric acid in a PBS buffer (0.1 M, pH 7.0).
Figure 22:
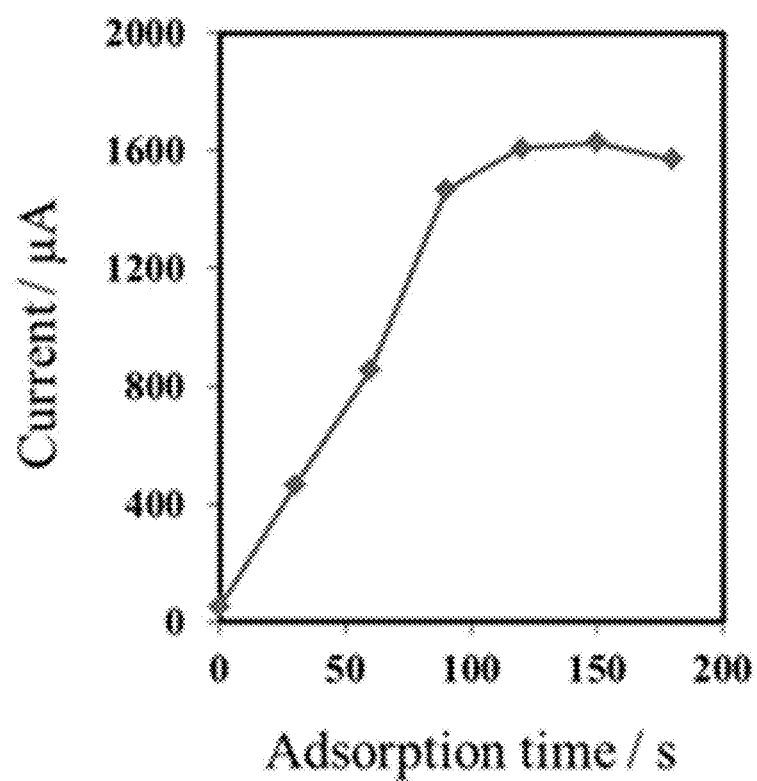
FIG. 22 shows a relationship between the current and the absorption time at the modified graphite electrode in a sample comprising 10 μM uric acid in a PBS buffer (0.1 M, pH 7.0).

All the possible parameters of the square wave voltammetry that could affect the electrochemical oxidation of the uric acid on the dERGO-GPE surface were studied. The amplitude was first varied between 0.020 V and 0.060 V. The oxidation peak current reached the maximum at 0.03 V and then continuously dropped with further increase of the amplitude (FIG. 20). The frequency also had a significant influence on the oxidation signal of the uric acid when the frequency was varied from 15 to 70 Hz. The maximum response was obtained at 50 Hz (FIG. 21). Finally, the adsorption time was investigated. The adsorption time has a significant effect on the strength of the oxidation signal. The current increased rapidly as the adsorption time increased and leveled off at 120 s and no further increase in current observed with time adsorption increase (FIG. 22). This enormous increase in current revealed the graphene layer on GPE surface, significantly enhanced dERGO-GPE capability for uric acid adsorption.

EXAMPLE 7

Calibration Curve and Detection Limit

Figure 23:
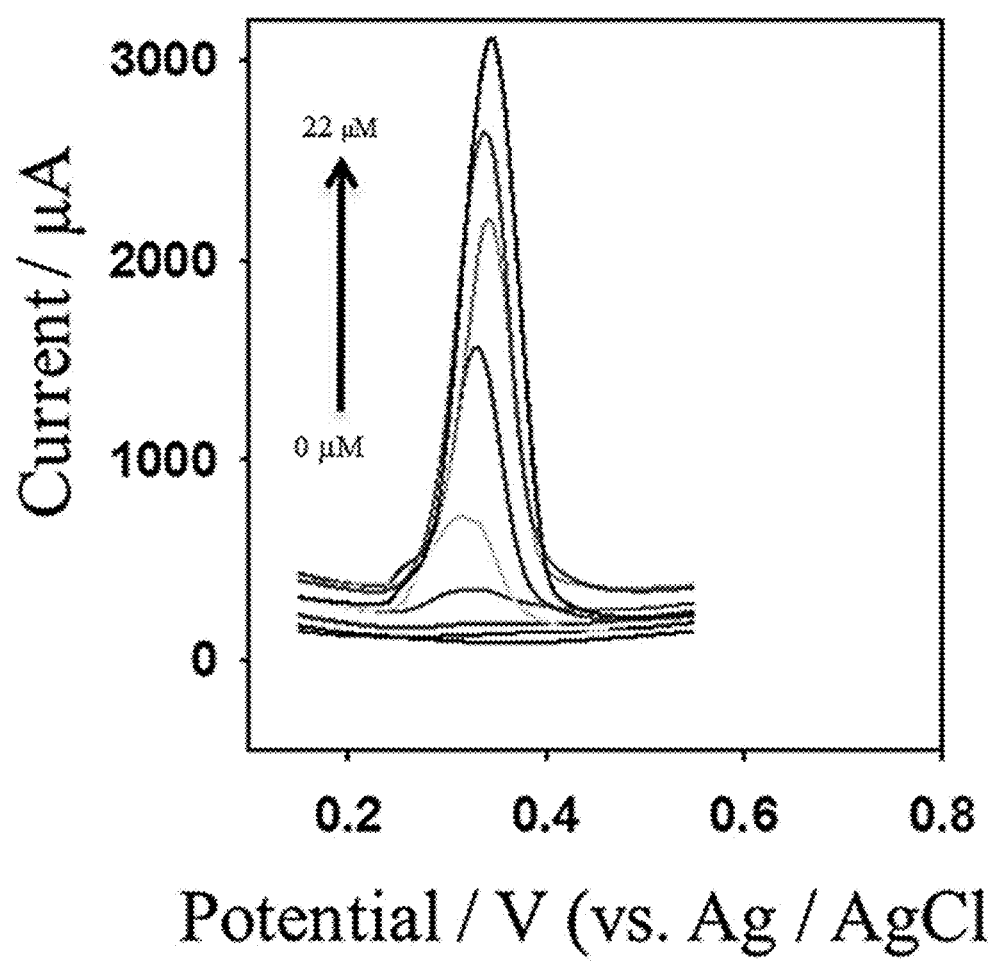
FIG. 23 is an overlay of square wave voltammograms at the modified graphite electrode in PBS buffer (0.1 M, pH 7.0) with various concentrations of uric acid: 0 μM, 0.2 μM, 0.5 μM, 2 μM, 6 μM, 10 μM, 14 μM, 18 μM, and 22 μM.
Figure 24:
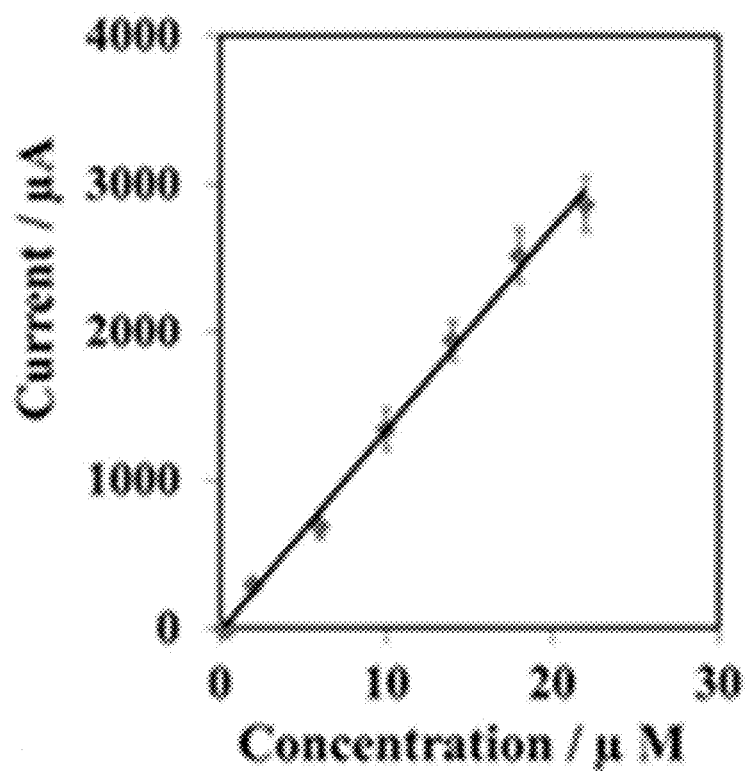
FIG. 24 shows a linear relationship between the peak current and the concentration of uric acid.
Figure 25:
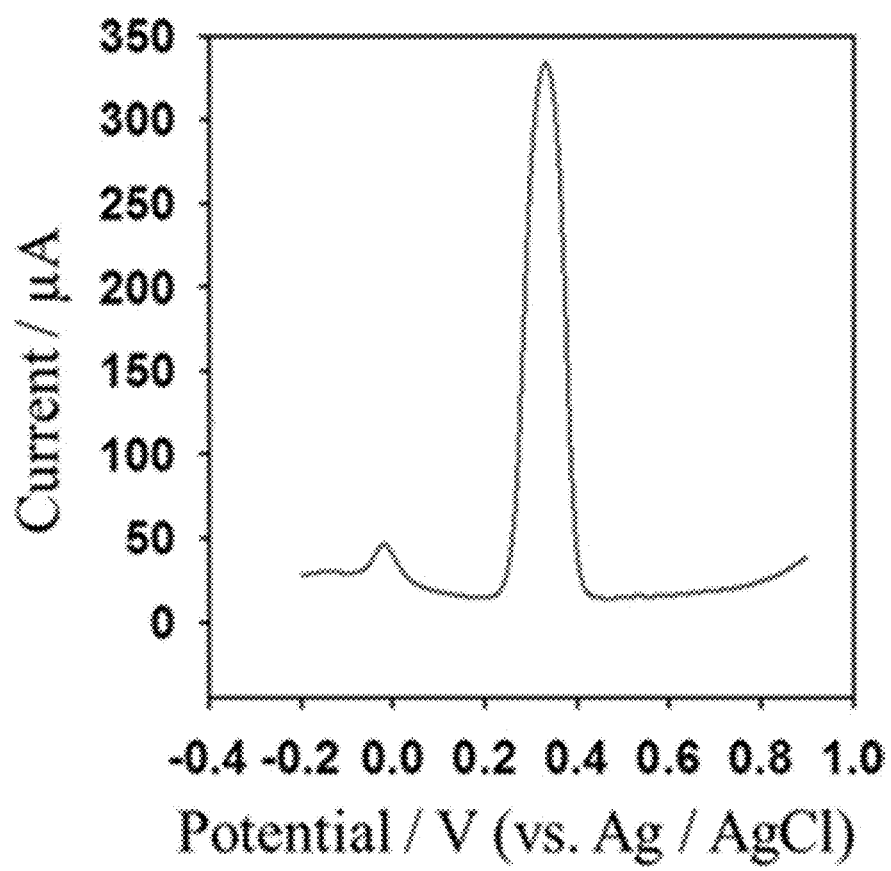
FIG. 25 is a square wave voltammogram of 500 μM ascorbic acid in the presence of 50 μM uric acid with square wave voltammetry parameters: amplitude 0.02 V, frequency 25 Hz, and adsorption time 30 s.
Figure 26:
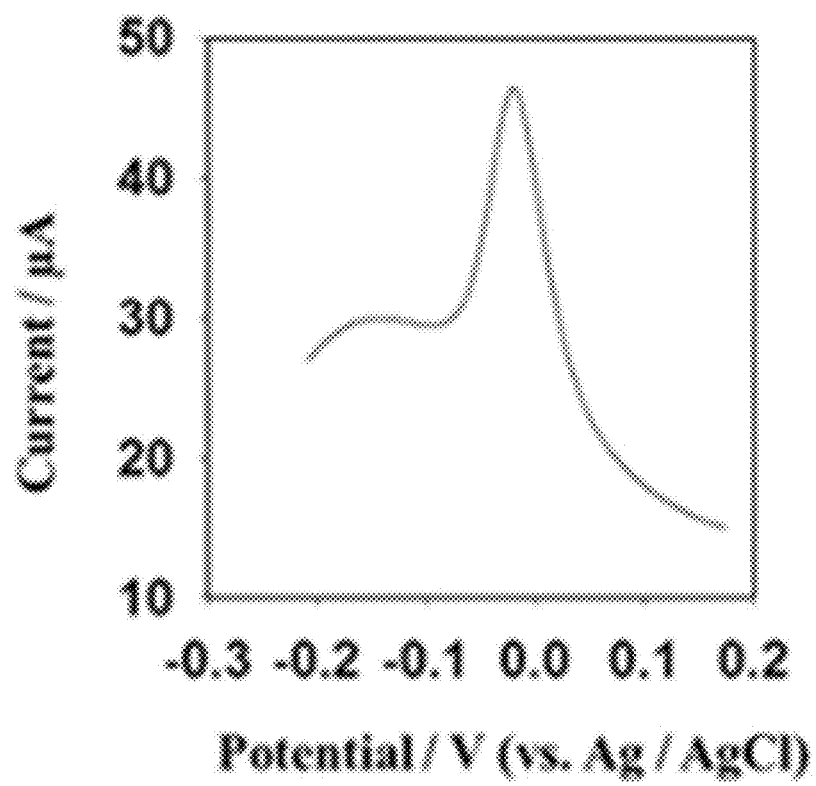
FIG. 26 is a square wave voltammogram of 500 μM ascorbic acid with square wave voltammetry parameters: amplitude 0.02 V, frequency 25 Hz, and adsorption time 30 s.
Figure 27:
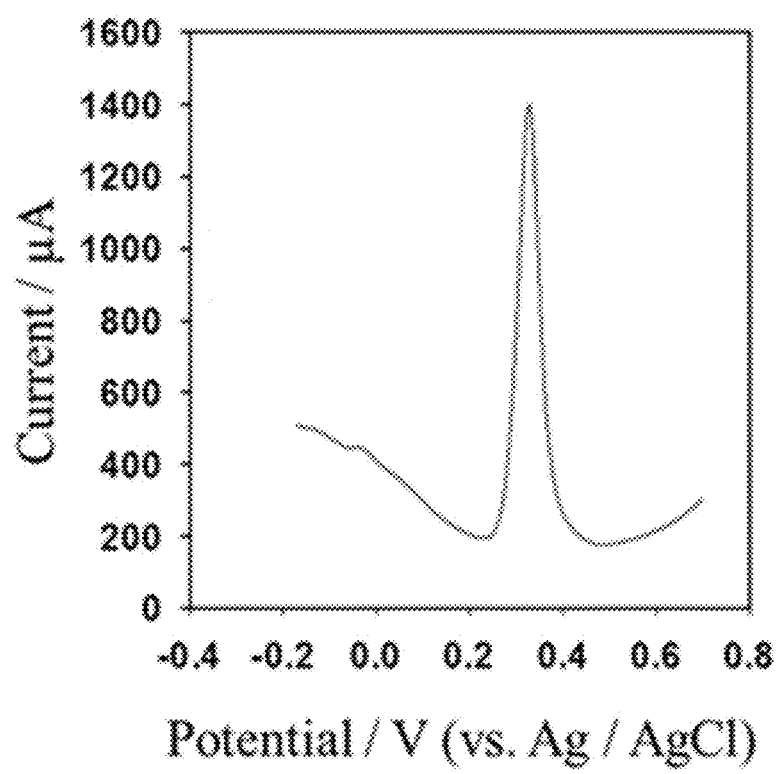
FIG. 27 is a square wave voltammogram of 500 μM ascorbic acid in the presence of 50 μM uric acid with square wave voltammetry parameters: amplitude 0.03 V, frequency 50 Hz, and adsorption time 120 s.
Figure 28:
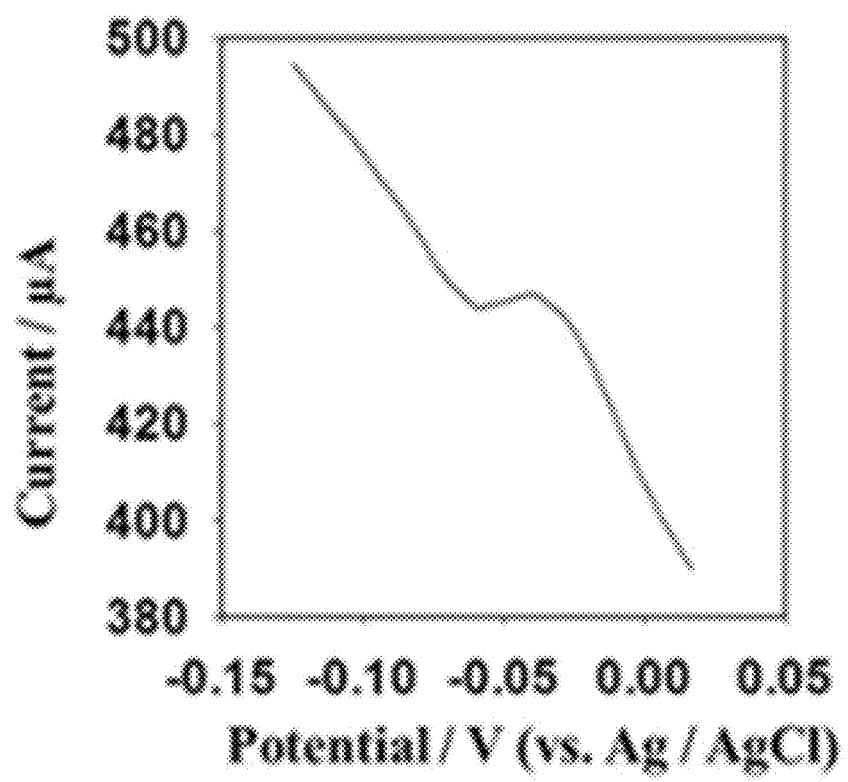
FIG. 28 is a square wave voltammogram of 500 μM ascorbic acid with square wave voltammetry parameters: amplitude 0.03 V, frequency 50 Hz, and adsorption time 120 s.

The oxidation of uric acid was performed with the dERGO-GPE at these conditions for SWV: 0.03 V amplitude, 50 Hz frequency and 120 s adsorption time (FIG. 23). The linear relationship was observed between 0.2 μM and 22 μM uric acid with a regression constant of 0.996. (FIG. 24) A linear equation yielded by the calibration curve is: (μA)=136.08 $C_{UA}$ (μM)−29.914. For dERGO-GPE, the limit of quantification was 0.2 μM and the limit of detection was 0.037 μM which is better than most of the reported electrodes modified to contain graphene (Table 2). In these cases, the glassy carbon electrode (GCE) is modified to contain graphene or graphene composite. These methods are time-consuming due to the number of steps involved in the modification of the electrode. X. Wang et al. fabricated a palladium nanoparticle/graphene/chitosan modified GCE for uric acid detection with a limit of detection 0.17 μM and the preparation of the electrode took 24 hours (X. Wang, M. Wu, W. Tang, Y. Zhu, L. Wang, Q. Wang, P. He, J. Electroanal. Chem. 695 (2013) 10-16, incorporated herein by reference in its entirety). Y. Xue et al. introduced a poly (diallyl dimethyl ammonium chloride)-graphene nanosheets modified GCE with a detection limit 0.1 μM. This modified electrode is prepared by a time-consuming process has several steps (Y. Xue, H. Zhao, Z. Wu, X. Li, Y. He, Z. Yuan, Biosens. Bioelectron. 29 (2011) 102-108, incorporated herein by reference in its entirety). Z. Zhang and J. Yin prepared a sensitive partially electro-reduced graphene oxide modified GCE with a detection limit of 0.05 μM and took 12 hours of preparation (Z. Zhang, J. Yin, Electrochim. Acta. 119 (2014) 32-37, incorporated herein by reference in its entirety). These modified GCE are prepared by the same method of casting of the graphene dispersion/solution onto the surface of the glassy carbon electrode and then dried at room temperature (Y. Li, G. Ran, W. J. Yi, H. Q. Luo, N. B. Li, Microchim. Acta. 178 (2012) 115-121, incorporated herein by reference in its entirety). A major issue with the casting method is that it is hard to control the thickness of the graphene layer. In addition, for all these references, several steps are involved in the preparation of the graphene composite which was then cast on the surface of the GCE.

In this work, the control of the coating thickness is easier because graphene oxide is reduced directly onto the surface of GPE. In addition, the dERGO-GPE has a lower limit of detection (0.037 μM) than the reported modified GCE indicated that graphene oxide is more efficiently reduced on the GPE surface.

TABLE 2

Comparison of the dERGO-GPE with other graphene modified electrodes

| Electrode | Technique | Electrode modification time (h) | LOQ (μM) | LOD (μM) | Ref. |
|---|---|---|---|---|---|
| Screen-printed graphene electrode | DPV | 1.16 | 0.8 | 0.2 | 1 |
| Pd NPs/graphene/chitosan/GCE | DPV | 24 | 0.5 | 0.17 | 2 |
| Au NPs-β-cyclodextrin graphene/GCE | SWV | 1.2 | 0.5 | 0.21 | 3 |
| Graphene Sheet-PTCA/GCE | DPV | C* | 4 | 0.92 | 4 |
| Neutral red-functionalized graphene nanosheets/GCE | Amperometry | C* | 0.12 | 0.062 | 5 |
| partially electro-reduced graphene oxide/GCE | SWV | 12 | 0.1 | 0.05 | 6 |
| Graphene poly(acridine red)/GCE | DPV | C* | 0.8 | 0.3 | 7 |
| $Pd_3Pt_1$/PDDA-Reduced Graphene Oxide/GCE | DPV | C* | 4 | 0.1 | 8 |
| PDDA-Graphene nanosheets/GCE | DPV | — | 0.5 | 0.1 | 9 |
| Directly electrochemically reduced graphene oxide/GPE | SWV | 0.46 | 0.2 | 0.037 | This work |

DPV = differential pulse voltammetry
SWV = square wave voltammetry
C* = certain amount of the graphene oxide composite cast on the surface of the GCE and dried but time is not mentioned.
1. J. Ping, J. Wu, Y. Wang, Y. Ying, Biosens. Bioelectron. 34 (2012) 70-76
2. X. Wang, M. Wu, W. Tang, Y. Zhu, L. Wang, Q. Wang, P. He, J. Electroanal. Chem. 695 (2013) 10-16
3. X. Tian, C. Cheng, H. Yuan, J. Du, D. Xiao, S. Xie, M. Choi, Talanta. 93 (2012) 79-85
4. W. Zhang, Y. Chai, R. Yuan, S. Chen, J. Han, D. Yuan, Anal. Chim. Acta. 756 (2012) 7-12
5. J. Song, J. Qiao, S. Shuang, Y. Guo, C. Dong, J. Mater. Chem. 22 (2012) 602-608
6. Z. Zhang, J. Yin, Electrochim. Acta. 119 (2014) 32-37
7. Y. Li, G. Ran, W. J. Yi, H. Luo, N. Li, Microchim. Acta. 178 (2012) 115-121
8. J. Yan, S. Liu, Z. Zhang, G. He, P. Zhou, H. Liang, L. Tian, X. Zhou, H. Jiang, Colloids Surf. B. Biointerfaces. 111 (2013) 392-397
9. Y. Xue, H. Zhao, Z. Wu, X. Li, Y. He, Z. Yuan, Biosens. Bioelectron. 29 (2011) 102-108
References 1-9 are each incorporated herein by reference in its entirety.

EXAMPLE 8

Application and Interferences

The dERGO-GPE sensor was applied to a urine sample collected from a healthy person and diluted with 0.1 M PBS. A sharp peak was observed at 0.327 V. It was confirmed by spiking of 8, 10, 12 µM of uric and the peak current increased linearly. The recoveries of the spiked uric acid lie between 98.2 and 105% (Table 3). The real sample has a number of ions, proteins and interfering species: the good recoveries indicated the developed electrode is foul free and could cope with real sample interferences. Ascorbic acid is the most commonly observed interfering species in the quantification of uric acid. It has been observed under conditions of SWV (25 Hz frequency, 0.02 V amplitude, and 30 s adsorption time), a prominent well-defined peak of the 200 µM ascorbic acid was observed. The preferred conditions for the detection of uric acid did not facilitate the oxidation of the ascorbic acid, and a small peak of ascorbic acid was observed. Although ascorbic acid is 50 times more concentrated than uric acid, there was just a 6% variation in the oxidation peak current for uric acid. Moreover, other interferences, such as 50 µM L-methionine, 50 µM L-alanine, 20 µM L-phenylalanine, 10 µM fructose, and 10 µM glucose were also studied with 10 µM of uric acid. The current variation observed varied from 5 to 12%. This small variation of current indicated, the dERGO-GPE has the capability to behave well in the presence of interfering species and remain foul free even at a much higher concentration of the ascorbic acid. The interfering studied indicated the interfering species and the high concentration of ascorbic acid do not affect the sensitivity of the electrode for uric acid. Therefore, the dERGO-GPE is a valuable tool for the sensitive detection of the uric acid in the urine due to low cost, fast, good linear range, high sensitivity and low limit of detection.

TABLE 3

Recovery of spiked uric acid in the urine sample

| Sr # | Found (µM) | Added (µM) | Recovered (µM) | Percent recovery |
| --- | --- | --- | --- | --- |
| 1 | 5.15 | 8 | 7.90 | 98.75 |
| 2 | 5.15 | 10 | 9.82 | 98.2 |
| 3 | 5.15 | 12 | 12.71 | 105 |

The invention claimed is:

1. A method for detecting uric acid, comprising:
   immersing a modified graphite electrode comprising a graphite electrode with an outer surface and a coating on the outer surface of the graphite electrode, wherein the coating consists of wrinkled layers of electrochemically reduced graphene oxide having hydroxyl groups, and the modified graphite electrode has an electroactive surface area in a range of 0.03-0.6 cm$^2$, a reference electrode, and a counter electrode in an aqueous sample comprising 0.02-1,000 µM uric acid; and
   applying a square wave potential to the aqueous sample.

2. The method of claim 1, wherein the reference electrode is Ag/AgCl, and the counter electrode comprises platinum.

3. The method of claim 1, wherein the square wave potential has an amplitude in a range of 0.01-0.1 V, a frequency in a range of 10-100 Hz, and an adsorption time in a range of 10-240 s.

* * * * *